United States Patent
Shea et al.

(10) Patent No.: US 9,332,899 B2
(45) Date of Patent: May 10, 2016

(54) ELECTRONIC EYE MARKING/REGISTRATION

(71) Applicant: Clarity Medical Systems, Inc., Pleasanton, CA (US)

(72) Inventors: William Shea, Pleasanton, CA (US); Yan Zhou, Pleasanton, CA (US)

(73) Assignee: CLARITY MEDICAL SYSTEMS, INC., Pleasanton, CA (US)

( * ) Notice: Subject to any disclaimer, the term of this patent is extended or adjusted under 35 U.S.C. 154(b) by 401 days.

(21) Appl. No.: 13/950,193

(22) Filed: Jul. 24, 2013

(65) Prior Publication Data

US 2014/0125949 A1  May 8, 2014

Related U.S. Application Data

(60) Provisional application No. 61/723,254, filed on Nov. 6, 2012.

(51) Int. Cl.
| | | |
|---|---|---|
| *A61B 3/10* | (2006.01) | |
| *A61B 3/00* | (2006.01) | |
| *A61B 3/103* | (2006.01) | |
| *A61B 3/117* | (2006.01) | |
| *A61B 3/036* | (2006.01) | |

(52) U.S. Cl.
CPC ............ *A61B 3/0058* (2013.01); *A61B 3/0025* (2013.01); *A61B 3/0041* (2013.01); *A61B 3/036* (2013.01); *A61B 3/103* (2013.01); *A61B 3/1035* (2013.01); *A61B 3/1176* (2013.01)

(58) Field of Classification Search
CPC ...... A61B 3/1015; A61B 3/102; A61B 3/103; A61B 3/1035; A61B 3/117; A61B 3/1176
USPC ........................... 351/205, 210, 212, 246, 221
See application file for complete search history.

(56) References Cited

U.S. PATENT DOCUMENTS

| | | | |
|---|---|---|---|
| 8,437,076 B2 * | 5/2013 | Takanashi | A61B 3/132 351/216 |
| 2010/0110379 A1 | 5/2010 | Zhou et al. | |
| 2010/0152487 A1 | 6/2010 | Sugiyama et al. | |
| 2011/0202044 A1 * | 8/2011 | Goldshleger | A61B 3/102 606/4 |

OTHER PUBLICATIONS

SensoMotoric Instruments GmbH; (SMI) Surgery Guidance brochure; ebook; Aug. 31, 2011; 6 pages.
International Search Report issued in connection with corresponding International Application No. PCT/US2013/056510, mailed Nov. 14, 2013, 1 page.

* cited by examiner

*Primary Examiner* — Huy K Mai
(74) *Attorney, Agent, or Firm* — Kilpatrick Townsend & Stockton LLP

(57) ABSTRACT

One embodiment is a method for finding, calculating and electronically marking a reference axis for astigmatism correction/neutralization of a patient eye during a refractive surgery.
The reference axis for astigmatism correction/neutralization can be determined intra-operatively based on one or more eye property measurements together with simultaneous recording a live eye image. The determined reference axis of astigmatism correction/neutralization can be updated and registered with one or more land mark(s) of the recorded eye image(s); and overlaid onto a live image of the eye. Another embodiment is a method of calculating and displaying in real time compensated refractive errors of the eye under operation with refractive components due to temporary surgically induced factors removed and refractive components due to surgeon-induced factors added.

49 Claims, 12 Drawing Sheets

ELECTRONIC EYE MARKING/REGISTRATION

RELATED APPLICATION

This application claims priority from provisional application No. 61/723,254 entitled Electronic Eye Marking/Registration filed Nov. 6, 2012 which is incorporated by reference for all purposes.

TECHNICAL FIELD OF THE INVENTION

One or more embodiments of the present invention relate generally to electronic eye marking/registration for vision correction procedure(s). In particular, the embodiments are related to determining a reference axis for astigmatism, astigmatism correction and electronically marking/registering/recording custom indicator(s) that tracks and overlays a live image of an eye.

BACKGROUND OF THE INVENTION

In a traditional cataract refractive surgery, the refractive astigmatic axis of the cornea anterior surface, the cornea, or the eye of a patient is measured or determined prior to surgery. In the following the term astigmatic axis defines the location of the axis or meridian of an astigmatic eye. A mark, (using ethylene blue marker, for example), identifying the astigmatic axis is then typically made on the sclera before or during the surgery to guide a surgeon in correcting the eye's astigmatism. For example, when performing a limbal relaxing incision (LRI) or corneal relaxing incision (CRI), the mark can guide the surgeon in determining where to make the incision. If a toric intra-ocular lens (IOL) is implanted, the mark can guide the surgeon in rotating the toric IOL to a desired orientation.

Traditional hand based astigmatic axis marking using a surgical marker pen generally is not accurate and/or precise as the thickness of the pen mark along with the fact that the mark "bleeds"/wicks out over a wider area causes additional meridian error covering an angular range of several to many degrees. In addition, the astigmatic axis measurement which is generally based on keratometry/keratoscopy or corneal topography does not take into account the contributions to astigmatism from the posterior corneal surface and potentially the contribution from the crystalline lens. Furthermore, a whole eye astigmatic axis measurement can have contribution from an astigmatic crystalline lens. All these can lead to unaccounted and uncorrected astigmatism error in a post-operative eye.

In light of the above, there is a need in the art for a better approach to more accurately determine a target axis of astigmatism correction or neutralization in a cataract refractive surgery such that any unaccounted astigmatism can be optimally corrected.

SUMMARY OF THE INVENTION

One or more embodiments of the present invention satisfy one or more of the above-identified needs in the art. In particular, one embodiment of the present invention is a method for electronically marking a reference astigmatism correction/neutralization axis of a patient eye during a refractive surgery, comprising the steps of measuring the property of an eye; simultaneously capturing and displaying a live eye image; determining the astigmatism correction/neutralization axis of the eye based on the eye property measurement and the concurrent live eye image; registering the astigmatism correction/neutralization axis with the live eye image; and electronically marking/registering custom indicator(s) of the astigmatism correction/neutralization axis that tracks and overlays the live image of the eye.

In another embodiment, the astigmatism correction/neutralization axis overlays an image of the eye that has been previously recorded.

In another embodiment, electronic marking directly on the live eye image of an astigmatism correction/neutralization axis is performed without the use of any hardware that projects or injects an angular measurement reticle onto either the eye or an image sensor that captures an image of the eye.

In another embodiment, real time intra-operative measurements of eye optical properties are displayed in real-time together with a live image of the eye of the patient. Examples of intra-operative measurements include the amount of sphere or spherical refractive error, astigmatism or cylinder or cylindrical refractive error, and the axis angle of the astigmatism. These intra-operative measurements can be compared with pre-operative measurement data and used to calculate a reference axis for astigmatism correction/neutralization. For example, this reference axis for astigmatism correction/neutralization can be the astigmatic axis of an aphakic eye, i.e. when the natural crystalline lens of the patient eye is removed. This astigmatism correction/neutralization axis can also be a target axis for best astigmatism neutralization/correction that might have taken into consideration surgical procedure (or factor) induced aberrations or even surgeon-practice induced change in the astigmatic property of the eye.

The reference axis can be determined intra-operatively at any point during cataract refractive surgery. For examples, prior to making a surgical incision a reference axis measurement can be taken. Another reference axis measurement can be taken right after a procedural step such as making an incision, or it can be taken with the eye in an aphakic state. The reference axis can also be updated real time during the refractive surgery. The astigmatism correction/neutralization axis is ideally the target axis for the alignment of a rotatable toric IOL. Also the astigmatism correction/neutralization axis is referenced by an LRI/CRI or a femtosecond laser procedure so that after all surgical wounds of the operated eye have healed the remnant astigmatism of the post-operative eye is minimized or corrected for the patient's target refraction.

In another embodiment, the step of calculating the astigmatism correction/neutralization axis of the eye intra-operatively can be further divided into more steps depending on if there is any significant change to the axis and magnitude of the astigmatism of the eye before, during (especially as the surgery is on-gong) and after the refractive surgery.

In another example embodiment, pre-operative eye property measurement data are compared with real time intra-operative eye property measurement data and the measurement data are used to further improve the astigmatism correction/neutralization outcome. In this respect, a pre-operative measurement of keratometry/keratoscopy or corneal topography or OCT (optical coherence tomography) or wavefront or auto-refraction or a combination of two or more of these measurements can be compared with an intra-operative measurement of keratometry/keratoscopy or corneal topography or OCT (optical coherence tomography) or wavefront or auto-refraction or a combination of two or more of these measurements. The changes in the optical property of the eye such as changes to spherical or cylindrical refractive errors resulting from surgical factors can be determined to enable the calculation of a true target astigmatism correction/neutralization axis.

In still another example embodiment, the comparison of the pre-operative eye property measurement(s), including biometry, with the intra-operative eye property measurement(s) is used also for the further correction of spherical refractive error in addition to the correction of cylindrical refractive errors so that an optimized intra-ocular lens (IOL), including a monofocal IOL, a bi-focal or tri-focal or multi-focal IOL, and a toric IOL, can be selected and also confirmed.

In still another example embodiment, the comparison of data can include not only pre-operative eye property measurement(s) and intra-operative eye property measurement(s) but also post-operative measurement(s) after the operated eye has completely healed and these data can be used to enable and/or enhance nomogram(s) for the selection and confirmation of IOLs.

In still another example embodiment, the target astigmatism correction/neutralization axis is associated with and reference to a post-operative wound-healed eye. A real time target refraction of the eye under operation but referenced to a post-operative wound-healed eye is displayed also. In other words, instead of a real time display of the current refraction of the eye under operation, what is presented to the surgeon is a virtual real time display of the target astigmatism correction/neutralization axis and the target refraction of a post-operative eye when its wound(s) has (have) healed.

Additional features and advantages will be apparent in view of the following detailed description and appended drawings.

DETAILED DESCRIPTION

Figure 1:
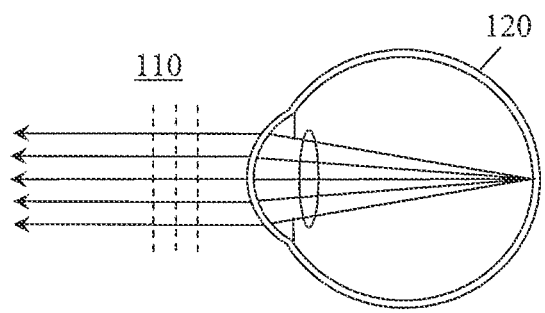
FIG. 1 shows planar wavefront coming out from an emmetropic eye that is in a relaxed state.

In one or more embodiments of the present invention, an image of the patient eye and an electronically marked reference axis for astigmatism correction/neutralization is presented to a surgeon during eye surgery without requiring any additional reticle projection hardware to be combined with a surgical microscope. In other embodiments of the present invention, the astigmatism correction/neutralization axis is more accurately and/or precisely determined by taking into consideration the changes in the astigmatic property of a patient eye before, during and after a refractive surgery. Furthermore, the electronically generated custom indicator(s) of the astigmatism correction/neutralization axis is (are) overlaid onto and registered with a live image of a patient eye on a display.

In the following discussion various types of surgically induced factors will be discussed and various methods of compensating these factors will be described. To simplify the following discussion the various surgically induced factors will be roughly divided into three categories.

The first category is temporary surgically induced factors that result from steps taken during the surgery, such as the insertion of the eye opening speculum that induce changes in refractive state/measurements of the eye taken during the surgery but will disappear after the surgery is completed. For example, the insertion of the speculum will distort the cornea while the speculum is in place but when the speculum is removed the cornea will return to its normal shape and no or very little refractive changes will persist. The surgically induced component of astigmatism caused by temporary surgically induced factors is referred to as temporary surgically induced astigmatism.

The second category is non-temporary surgically induced factors which result from changes to the refractive state of the eye such as the incisions made in the cornea and other eye trauma that occur during the surgery. These changes will remain at the time the surgery is just completed. The surgically induced component of astigmatism caused by non-temporary surgically induced factors is referred to as non-temporary surgically induced astigmatism.

The third category is wound healing induced factors, which result from changes to the refractive state of the eye as the eye recovers from the surgery. These changes will exhibit themselves from the moment the surgery is just completed to after the eye has completely recovered from the surgery in several weeks or months. The wound healing induced component of astigmatism caused by wound healing induced factors is referred to as wound healing induced astigmatism.

The second and third categories are often considered together as surgeon-induced factors or surgeon specific surgically induced factors, which result from surgical techniques unique to a particular surgeon such as the habitual placement and characteristics of the incision made by a particular surgeon. The surgically induced component of astigmatism caused by surgeon-induced factors is referred to as surgeon (or surgically)-induced astigmatism (SIA).

In other embodiments of the present invention, real time eye refraction or wavefront measurement results are presented to the surgeon. The real time measurement can be of the current eye under operation with the influence of current surgical factors. On the other hand, the real time measurement can also be of a virtual relaxed and wound-healed eye with the influence of surgical factors already digitally removed. In other words, the real time displayed refraction or wavefront results are already corrected for the influence of temporary and surgeon specific surgically induced factors, and therefore are referenced to an eye as if the eye is relaxed without the influence of temporary and surgeon specific surgically induced factors. In the latter case, surgical factors, including surgeon induced refractive errors, have been taken into consideration in calculating the real time refraction referenced to a fully healed eye without the influence of temporary and surgeon specific surgically induced factors as the surgery is on going. What the real time displayed refraction of the eye is telling the surgeon is how far his/her surgical outcome is from a true targeted refraction (such as emmetropia) of the patient eye after the eye is healed.

An eye without any optical aberration is called an emmetropic eye and the normal aberration-free vision or sight is called emmetropia. In such an eye with perfect vision, the rays of light from a distant object can be brought into sharp focus on the retina while the eye is relaxed. This is what you want with laser or other vision correction procedures. Since for a distant object, the wavefront entering a relaxed emmetropic eye can be considered planar, when the light ray propagation direction is reversed, i.e. when light rays emitted from a point source near the fovea travels backward through the eye optics system and leaves the eye, the wavefront is also planer. FIG. 1 shows the planar wavefront 110 returned from a relaxed emmetropic eye 120.

Figure 2:
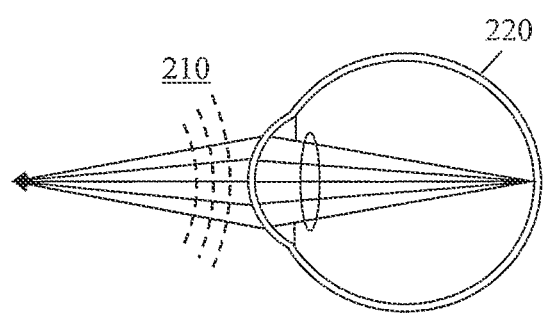
FIG. 2 shows convergent spherical wavefront coming out from a myopic or nearsighted eye.
Figure 3:
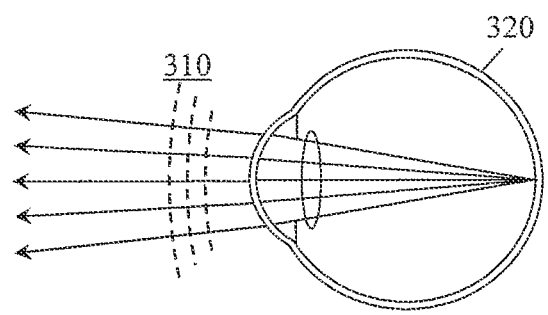
FIG. 3 shows divergent spherical wavefront coming out from a hyperopic or farsighted eye.

Eye aberrations are traditionally classified as low order and high order. Low-order aberrations include defocus (also called spherical refractive error) and astigmatism (also called cylindrical refractive error). More familiar names for two different types of defocus are nearsightedness (myopia) and farsightedness (hypermetropia or hyperopia). These refractive errors can be measured with an auto-refractor, and they make up about 85 percent of all aberrations in an eye. When light rays emitted from a point source near the fovea travel backward through the eye optics system that has defocus and leaves the eye, the wavefront is either spherically convergent or spherically divergent. FIG. 2 shows the convergent spherical wavefront 210 coming out from a myopic or nearsighted eye 220 and FIG. 3 shows the divergent spherical wavefront 310 coming out from an hyperopic or farsighted eye 320.

If there is no astigmatism caused by the cornea, the cornea of the eye is shaped like the cross section of a baseball cut in half. The curvature or steepness of the half-dome is the same all the way around. Compare this to a cornea which is similar to a football cut in half lengthwise (in the long direction, through both pointy ends). The curvature of the cornea in the long direction (along the seams) is not as steep as along the short direction. Such a cornea focuses light, not at a single point, but at 2 points. Someone who has uncorrected astigmatism may see images that are fuzzy and doubled. A cornea shaped like a football, cut lengthwise, has astigmatism.

In an eye with astigmatism, the rays of light from a distant object are brought into focus along two perpendicular orientation directions or meridians at two different points, for example, one on the retina and the other, behind the retina. This can be the case of an eye with a cornea that has astigmatism, a non-uniform curvature like the football cut lengthwise. The two different curvatures results in two different focal points. There are several different combinations of astigmatism, depending on where the focal points are located. Examples include:

Simple myopic astigmatism: One point in front of retina, the other on the retina;
Compound myopic astigmatism: Both points of focus in front of the retina;
Simple hyperopic astigmatism: One point behind the retina, the other on the retina;
Compound hyperopic astigmatism: Both points of focus behind the retina;
Mixed astigmatism: One point in front of the retina, the other behind the retina;

Often, when astigmatism occurs inside the eye as well as at the cornea, the astigmatism inside the eye can be just opposite in amount to the corneal astigmatism. The two forms of astigmatism can thus cancel each other and leave the eye with no significant amount of astigmatism.

An astigmatic eye generally has two different meridians, oriented at 90° to each other, which cause images to focus in different planes for each meridian. The meridians can each be myopic, hyperopic, or emmetropic. The correction for astigmatism is generally a cylindrical or toric lens with different light-ray-focusing-powers at different particular orientation directions. The difference of the diopter power along the meridians is the astigmatism power.

The angular orientation of the meridian(s) of astigmatism is referenced to one or two 180 degree half circle(s). If the viewing direction is from an observer, for the upper half circle, the angular orientation is with the 0 degree mark placed at the right side of the patient eye and the degree numbers increasing along the upper half circle in an anti-clockwise direction. For the lower half circle, the angular orientation is with the 0 degree mark placed at the left side of the patient eye and the degree numbers increasing along the lower half circle in an anti-clockwise direction. The angular orientation of the meridian having the least power or the flatter principal meridian of the eye is defined as the axis of astigmatism.

Astigmatism is also described as "cylinder" power where the circular cylinder has a height axis perpendicular to the diameter of the circular cross sections and a width axis perpendicular to the first axis. The height axis of the cylinder measures no curvature and the width axis of the cylinder measures its curvature. The height axis is the axis of astigmatism.

Astigmatism causes images to be out of focus no matter what the distance. It is possible for an astigmatic eye to minimize the blur by accommodating, or focusing to bring the "circle of least confusion" onto the retina.

In order to correct astigmatism, the location of the axis of a cylindrical lens must be specified when it is placed before or inside the eye. In designating the angle of the axis, the observer faces the patient and the orientation angle zero is at the observer's left. The scale is read below the horizontal line with 90° at the bottom and 180° at the right.

For the case of an astigmatic eye or an eye with cylindrical refractive error, the wavefront coming out from a point light source near the fovea of the eye will no longer be rotationally symmetric relative to the optical axis and instead, the wavefront will have different spherical divergence or convergent along two different but mutually perpendicular azimuthal orientation directions.

Figure 4:
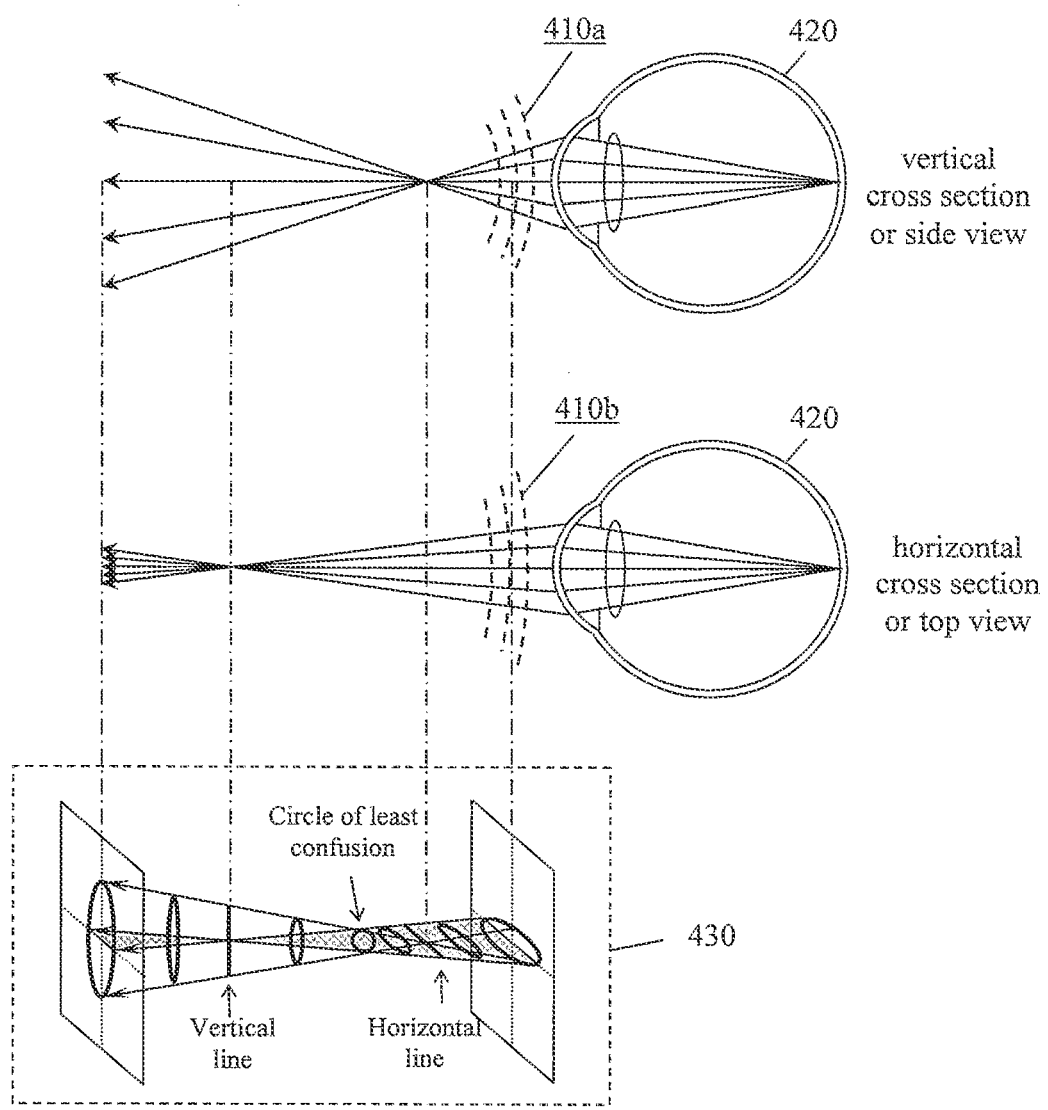
FIG. 4 shows the wavefront coming out from an eye that is nearsighted but also with astigmatism.

FIG. 4 shows the wavefront coming out from an eye 420 that is nearsighted but also with astigmatism (compound myopic astigmatism). Note that the degree of convergence of the wavefront after leaving the eye is different for the vertical (side view) and the horizontal (top view) cross sections. The vertical cross sectional wavefront 410a for the side view case is initially more convergent after the light rays leave the eye than the horizontal cross sectional wavefront 410b is for the top view case. Correspondingly, the beam shape will also no longer be purely conical with rotational symmetry around the optical axis. As shown by the three-dimensional illustration of 430, following the light propagation from the right to the left, the beam cross-sectional shape (perpendicular to the beam propagation direction) will change from a larger horizontal ellipse, to a horizontal line, to a smaller horizontal ellipse with a shorter major axis, to a circle of least confusion, to a smaller vertical ellipse with a shorter major axis, to a vertical line, then to a larger vertical ellipse.

It should be noted that visual acuity and visual performance are related to wavefront aberrations, but the metrics used to describe vision is not the same as a spectacle glass or contact lens prescription which can be taken to an optical shop to be filled. Vision is usually given in the Snellen format, for example, 20/40. For 20/40 vision, an object that can be clearly seen by a patient 20 feet away, can be clearly seen from 40 feet away by someone who has 20/20 vision. Therefore, someone with 20/400 vision has even worse vision; the larger the denominator or the second number, the poorer the vision. In the extreme, if the vision is even worse, such that a person cannot see the biggest letter "E" on the eye chart, the number of fingers that can be counted is a way of measuring vision. If someone has "counting fingers at 3 feet", it means the eye in question has worse than 20/400 vision, and can only identify the number of fingers held 3 feet away. The gold standard of perfect vision has been 20/20 vision, though there are patients capable of seeing better than "perfect". While most patients use both eyes together, vision is tested in each eye separately, as is the measurement of a person's prescription. The table below shows the relationship between visual acuity (in feet and meters) and refractive error in diopters, which is a unit of measurement of the optical power of a lens, equal to the reciprocal of the focal length measured in meters (that is, 1/meters).

| Visual Acuity in Feet | Visual Acuity in Meters | Refractive Error in Diopters |
|---|---|---|
| 20/20 | 6/6 | 0.00 |
| 20/30 | 6/9 | −0.50 |
| 20/40 | 6/12 | −0.75 |
| 20/50 | 6/15 | −1.00 |
| 20/70 | 6/20 | −1.25 |
| 20/100 | 6/30 | −1.50 |
| 20/150 | 6/45 | −2.00 |
| 20/200 | 6/60 | −2.50 |
| 20/250 | 6/75 | −3.00 |

In terms of prescription for vision correction, if an eye is just nearsighted, there will be a single negative diopter number. The minus sign indicates nearsightedness or myopia. The number that comes after the minus sign tells the amount or "severity" of the nearsightedness. For examples a −1.00 D means one (1.00 D) diopter of nearsightedness, a −5.25 D means 5.25 diopters or 5 and ¼ diopters of nearsightedness. This is more nearsighted than −1.00 D, and so thicker negative glasses are needed.

If an eye is just farsighted, there will be a single positive diopter number. The plus sign indicates farsightedness or hyperopia. The number that comes after the plus sign tells the amount or "severity" of the farsightedness. For examples, a +1.00 D means one diopter of farsightedness, a +5.75 D means 5.75 or 5 and ¾ diopters of farsightedness. This is more farsighted than +1.00 D, and so thicker positive glasses are needed.

If an eye has astigmatism, the numbers are harder to follow. There are actually 3 numbers in a prescription for an eye that has astigmatism. The general form is S+C×Axis. Both S and C can be either positive or negative numbers. S refers to what is called the "sphere" or spherical portion of the prescription. The C refers to the amount of astigmatism or cylindrical portion of the prescription. The Axis is a number anywhere between 0 and 180 degrees; this axis number tells where the difference in corneal curvature occurs or how the astigmatism is oriented or aligned. It is not enough to specify how much astigmatism there is, it is necessary to know where the difference in curvature is taking place, by giving coordinates. Accordingly, there are three numbers in a prescription for astigmatism of some kind and severity. The bigger the second number, C, the more astigmatism there is. There are several categories of astigmatism, and by analyzing the 3-numbered prescription, the exact type of astigmatism is specified. For examples, −2.00+1.50×180 means a minus 2 diopter of spherical refractive error with a plus 1.50 diopter of astigmatism at an axis of 180 degrees; +4.00+3.00×89 means a plus 4 diopter of spherical refractive error with a plus 3 diopter of astigmatism at an axis of 89 degrees.

Higher-order aberrations refer to other distortion acquired by a wavefront of light when it passes through an eye with irregularities of its refractive components (tear film, cornea, aqueous humor, crystalline lens and vitreous humor). Abnormal curvature of the cornea and crystalline lens may contribute to higher order aberrations (HOA). Serious higher-order aberrations also can occur from scarring of the cornea from eye surgery, trauma or disease. Cataracts clouding the eye's natural lens also can cause higher-order aberrations. Aberrations also may result when dry eye diminishes eye's tear film, which helps bend or refract light rays to achieve focus. Some names of higher order aberrations are coma, trefoil and spherical aberration. Higher order aberrations can be measured using a wavefront sensor and they make up about 15 percent of the total number of aberrations in an eye.

Traditionally, the astigmatic axis of the cornea anterior surface would be measured or identified pre-operatively using a keratometer/keratoscope or a corneal topographer; alternatively, the astigmatic axis of the whole eye would be measured or identified pre-operatively using an auto-refractor or a wavefront sensor. A surgeon would mark the astigmatic axis of either the corneal anterior surface or the whole eye based on these preoperative measurement(s) before or during a cataract surgery. This marking is then fixed during the surgery and is not updated. This conventional practice has limited accuracy and/or precision. Furthermore, each surgeon can also induce the so-called surgeon-induced-astigmatism. As a result, a post-operative eye may still have residual astigmatism. There is, therefore, a need to minimize or more ideally completely remove this residual astigmatism.

In one example embodiment, live continuous measurements of the optical property of a patient eye are made and the marking of a reference axis for astigmatism correction/neutralization is updated intra-operatively based on the quality of the measurement data and the transition of surgical stages. Using these measurements and deploying electronic marking, a live/recorded eye image/video display is created with the marking(s) registered with and overlaid onto the live/recorded eye image without the use of any additional hardware to project or inject an angular measurement reticle or alignment indicia.

Figure 5:
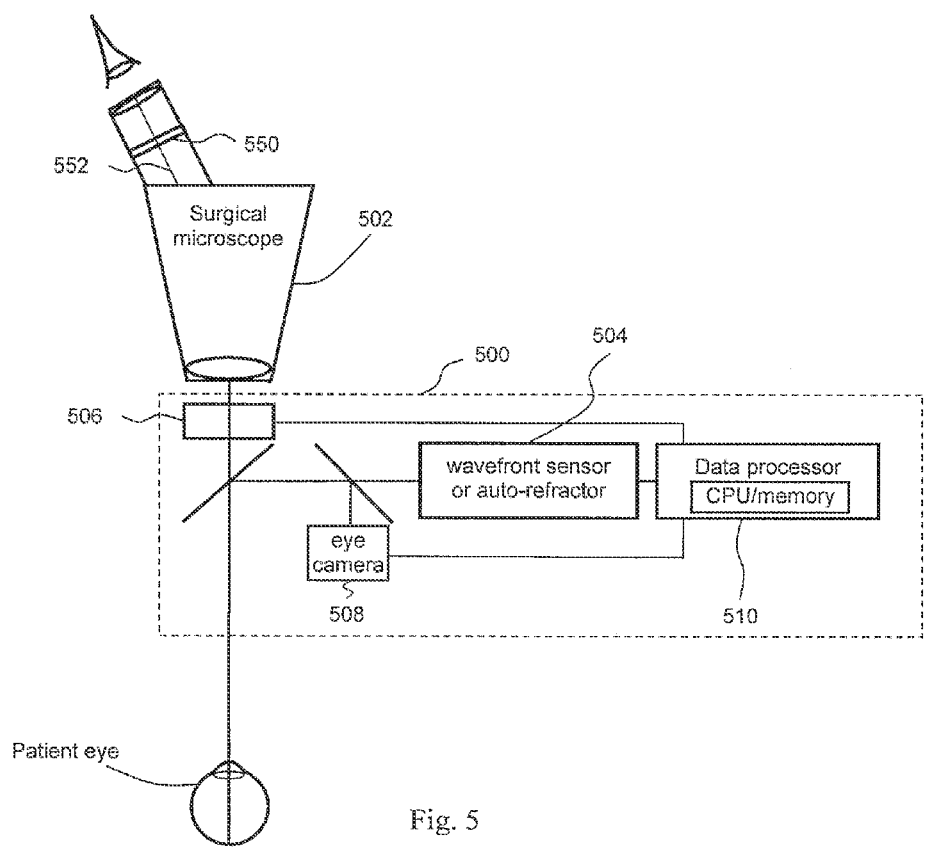
FIG. 5 is a block diagram of an example embodiment of a system suitable for use in various example embodiments.

FIG. 5 is a block diagram of a system used to practice various example embodiments. FIG. 5 depicts a module 500 that can be integrated or attached to the front end of a surgical microscope 502. The module includes a wavefront sensor or auto-refractor 504, an eye camera 508, and a data processor 510 including a CPU and a tangible memory, holding program code and data, and input and output ports. A corneal shape measurement device such as a keratometer/keratoscope, or cornea topographer or optical coherence topographer/tomographer (OCT) 506 can also be included. In addition, a display (not shown in FIG. 5) can also be electronically coupled to the data processor.

In this example the wavefront sensor 504 is a sequential wavefront sensor as described in commonly assigned U.S. Pat. No. 7,445,335 and U.S. patent application 20120026466, the eye camera 508 is a UI-1542LE-M which is an extremely compact board-level camera having 1.3 Megapixel resolution (1280×1024 pixels) and the corneal shape measurement device (506) is a Mastel illuminating surgical keratoscope. These particular devices are described by way of example, not limitation, and persons of skill in the art will be able to substitute other suitable devices as required.

In this example the surgical microscope includes a transparent display 550 located in the viewing optical path of the surgical microscope 552 so that various types of data can be displayed intra-operatively to the surgeon without the surgeon having to remove his eyes from the eyepieces of the surgical microscope. This feature is also referred as a "heads-up display".

Figure 6:
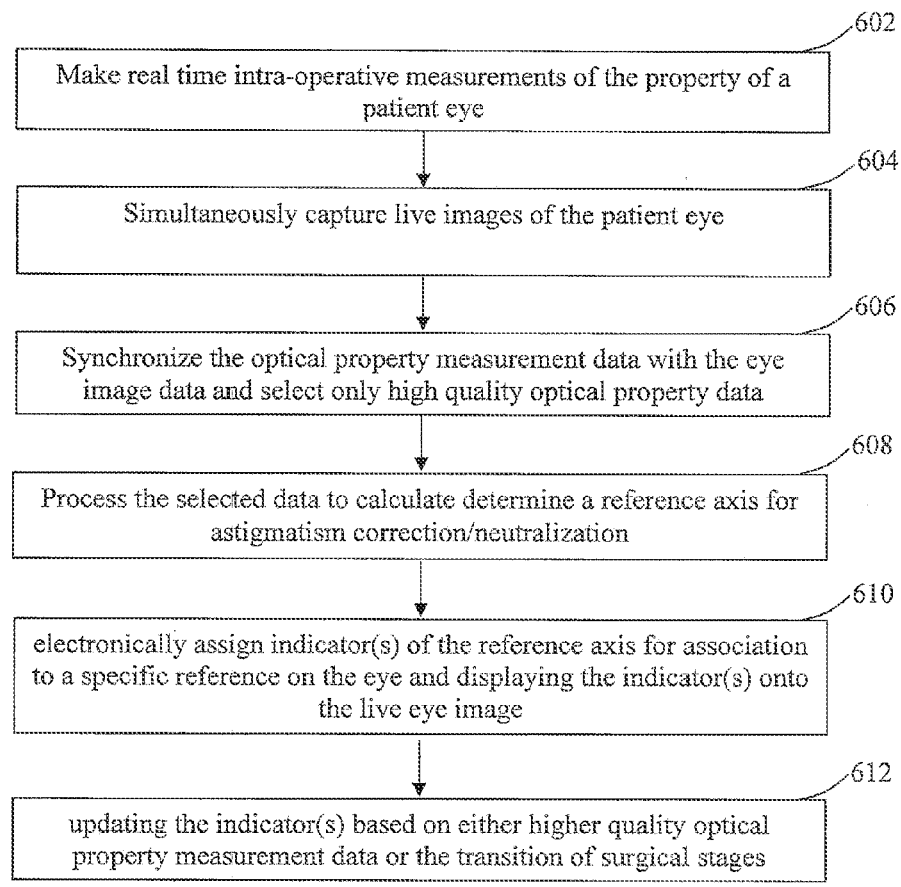
FIG. 6 shows one example method for electronically marking/registering a patient eye undergoing a refractive surgery without the use of any angular measurement reticle image injection or projection hardware.

FIG. 6 shows an example method for electronically marking/registering a patient eye undergoing a cataract refractive surgery. At step 602, continuous live, real-time intra-operative measurements of the optical properties of a patient's eye are made. Types of example measurements include autorefraction, aberrometry, wavefront, keratometry/keratoscopy, corneal topography or optical coherence topography/tomography or a combination of two or more of these measurements.

At step 604, live images of the eye are also simultaneously and continuously captured and/or recorded by the eye camera 508. In one example embodiment, the live eye image is also used to determine how well the eye is aligned with the optical axis of the instrument being used for the real-time intra-operative measurements of the optical properties of the eye.

At step 606, the live eye image frames are synchronized with the live eye optical property measurement data and the quality of the eye optical property measurement results are determined based on the synchronized eye image data or other eye alignment measurement data to select only high quality eye optical property measurement data. In an example embodiment, the eye camera 508 and wavefront sensor 504 are coupled to the data processor 510 and interfaced using standard off-the-shelf software compilers, UI builders, services, and drivers such as, for example, Microsoft Visual Studio Professional and the Microsoft DirectShow application programming interface (API), which is a media streaming architecture for Microsoft Windows, so that the software receives a continuous stream of data from both the video camera and wavefront sensor hardware. In another example embodiment, the eye camera 508 and keratometer/keratoscopy 506 are coupled to the data processor 510 and interfaced using standard off-the-shelf software compilers.

A measurement data quality judgement criterion can be established to ensure that only high quality eye optical property measurement data associated with well-aligned eye images are selected for follow-up data processing. The quality of the eye optical property measurement data can be based on a criterion taking into consideration the position range of the patient eye relative to the measurement device being used for making the real time intra-operative measurement and also the signal strength range of the eye optical property measurement.

At step 608, the selected data from the measurement of the optical property of the eye are processed to calculate indicator(s) (lines, arrows, blinking identifiers, for examples) of a reference axis for astigmatism correction/neutralization. In another example embodiment, the selected data are also processed to calculate surgical factor induced refractive errors, including especially, temporary and surgeon specific surgically induced astigmatisms.

At step 610, indicator(s) representing the reference axis for astigmatism correction/neutralization are electronically assigned for association to a specific reference on the synchronized eye image. The specific reference can be iris land mark(s), speculum, canthus, a surgically placed fiducial(s), or device fiducial(s), and others. At the same time, the indicator(s) can also be displayed onto the live eye image in the field of view of the surgical microscope with the indicator(s) referenced to the live eye image of the surgical microscope. In other words, the indicator(s) is (are) referenced to a recorded live eye image and hence tracked to real eye movement but the overlay can be done on a transparent display inside the surgical microscope that does not need to display a live eye image on the transparent display because a live eye image is already being presented by the microscope to the surgeon.

At step 612, the electronically assigned indicator(s) is (are) updated relative to the live eye images that are continuously being captured based on either higher quality eye optical property measurement data or the transition of surgical stages. For example, the electronically assigned indicator(s) can be updated based on if the eye is even better aligned relative to the eye optical property measurement device such as a real time wavefront sensor in terms of the eye's transverse as well as axial position within an even tighter range and/or if the data from the measurement(s) are of even higher quality in terms of the signal strength range as can be judged by a built-in data processing algorithm(s).

More likely, the update can and will be performed or effected at different stages of a cataract surgery by a built-in algorithm or the surgeon/nurse when a surgical stage transition occurs. In the following the term "phakic stage" refers to an eye having the natural crystalline lens in place, the term "aphakic stage" refers to an eye having the crystalline lens removed, and the term "pseudo-phakic stage" refers to an eye having the natural crystalline lens replaced by an intraocular lens (IOL). Examples of different surgical stages that can provide valuable eye optical property information include a pre-operative phakic stage before the application of an eye lid opening speculum, an intra-operative phakic stage after the application of eye lid opening speculum, an intra-operative aphakic stage when the natural crystalline lens is removed and the anterior chamber of the eye is filled/pressurized with viscoelastic liquid, and an intra-operative pseudo-phakic stage when an intra-ocular lens (IOL) is implanted and being aligned during the surgery.

The built-in algorithm, stored in the tangible memory and executed by the processor, can be configured to detect transitions between the various stages automatically and perform the necessary calculations to update the axes and refractive values displayed to the surgeon. Alternatively, the algorithm can respond to user input indicating the change in eye stage or indicating other events that occur during a procedure.

As an example, before the application of eye lid opening speculum, a whole eye wavefront aberrometry or auto-refraction measurement can be made when the eye is well aligned to determine the optical property of the eye at the pre-operative phakic stage. The measured astigmatism will have an astigmatic axis of the eye that can be initially marked as the electronically assigned indicator(s) on a live eye image and tracked to any further eye movement. An update of the electronically assigned indicator(s) or a second electronically assigned indicator(s) can be digitally drawn, after the occurrence of temporary surgically induced factors such as the application of a pair of eye lid opening speculum to the patient eye when the eye is well aligned. The second measured astigmatism can reveal any additional astigmatism component induced by the application of the speculum. The updated or second electronically assigned indicator(s) can be the astigmatic axis of the eye under the influence of the speculum or the astigmatic axis of the added but temporary astigmatism component induced by the speculum (i.e. the difference of the second and the first measured astigmatisms). If the difference in the astigmatism and/or the astigmatic axis angle of the eye between the two surgical stages is small, a single electronically assigned indicator will be sufficient. If, on the other hand, the difference in the astigmatism and/or the astigmatic axis angle of the eye between the two situations is relatively large, two indicators can be displayed using two different colors or line patterns to inform the surgeon that the application of the speculum has changed the cornea shape and as a result, there is temporary surgically induced astigmatism.

Alternatively, a single indicator of the temporary surgically induced astigmatism calculated/determined based on the two measurements can be displayed. Similarly, when the eye is in the aphakic state, a further update of the electronically assigned indicator(s) can be done to provide the surgeon with the information on the astigmatic axis of the cornea alone but under the influence of both temporary and non-temporary surgically induced factors such as the astigmatic axis of the cornea alone without the influence of the temporary surgically induced factors. Again, if the difference in the astigmatism or the astigmatic axis angle of the eye between this aphakic state and the previous one or two eye state(s) is small, the same single electronically assigned indicator will be sufficient. On the other hand, if the difference in the astigmatism or the astigmatic axis angle of the eye between this aphakic stage and the previous one or two eye stage(s) is large, an updated indicator calculated/determined based on the measurements of the two or three stages can be electronically marked on the live eye image and be tracked to any further movement of the eye.

In order to appreciate the importance of the need to consider the contribution of temporary and surgeon specific surgically induced factors to the optical property of an eye under operation, let us briefly review the well established vector analysis method for astigmatism and then take a look at a simple numerical example.

In the vector analysis method for astigmatism, each astigmatic contribution or component is considered as a vector with a magnitude and a direction. Owing to the fact that the axis of astigmatism repeats itself at 180°, while geometrical angles repeat after 360°, the problem is resolved by doubling the angle of astigmatism prior to calculations, and halving the angle after the calculation. The length of a vector represents the astigmatic dioptric value (diopter) of an astigmatic component, whereas the angle of a vector equals twice the astigmatic axis angle in the eye space as normally understood. For example, if two thin cylinder lenses are stacked on top of each other and obliquely crossed, the resultant astigmatism can be found using a double-angle vector diagram by adding the two vectors representing the two astigmatic components of the two cylinder lenses and then finding the length of the resultant vector and halving the angle of the resultant vector.

On the other hand, surgically induced astigmatism (SIA) can be found using the vector analysis method as well. It has been well established that the overall surgically induced astigmatism (SIA) is equal to the post-operatively measured astigmatism minus the pre-operatively measured astigmatism. In other words, using the double-angle vector diagram, the pre-operatively measured astigmatism represented by a vector $C_{pre}$ plus the surgically induced astigmatism (SIA) represented by a vector $C_{SIA}$ is equal to the post-operatively measured astigmatism represented by a vector $C_{post}$. Note that there might be different definitions in the post operative measurement, as it can be done right after the surgery is completed before or after the removal of eye lid opening speculum, or several weeks or months after the eye has completely healed from the surgery, so the measured astigmatism can be different depending on the definition or interpretation of post operative measurement. As different surgical factors can induce different astigmatism contributions or components, the induced astigmatism can therefore be further divided into different categories and components, including temporary, non-temporary and wound-healing. For example, the application of eye lid opening speculum can introduce a temporary astigmatic component (which we can label as temporary speculum induced astigmatism), the incision made on the cornea of a patient eye can introduce a non-temporary astigmatic component (which we can label as non-temporary cornea incision induced astigmatism), and eye recovery from the surgery can introduce a wound healing induced astigmatism, etc.

We can now take a look at a more detailed but simplified numerical example. Assume an eye at its phakic stage before the application of eye lid opening speculum and a keratometric/keratoscopic or wavefront measurement finds that the cornea or the eye has a first measured net astigmatism of 1.00 diopter magnitude at a meridian or astigmatic axis angle of 30° relative to the horizontal axis of the eye. A first reference axis can be initially marked in the form of a double arrow headed line oriented at 30° as the electronically assigned indicator on a live eye image to inform the surgeon that the phakic eye has an axis of astigmatism at the 30° orientation direction. In the double-angle vector diagram, this first measured astigmatic component can be represented by a vector $C_{1st-measured}$ pointing at an orientation angle of 60° (30° doubled is 60°) with respect to the x-axis as shown in FIG. 7.

If, after the application of eye lid opening speculum, the pressure on the cornea from the speculum causes the cornea to bend more along the vertical direction of the eye, then there will be an added temporary speculum induced astigmatic component of a certain dioptric value with a certain orientation angle as well as temporarily induced sphere or spherical refraction component. If an intra-operative keratometric or wavefront measurement of the same eye under the influence of the speculum shows that the measured net astigmatism of the cornea or the eye has a magnitude of 1.00 diopter at a meridian or astigmatic axis angle of 60° relative to the eye, then in the double-angle vector diagram, this second measured astigmatism can be represented by a vector $C_{2nd-measured}$ pointing at an orientation angle of 120° (60° doubled is 120°) as shown in FIG. 7. In the double-angle vector diagram, the net astigmatism as represented by the second vector $C_{2nd-measured}$ should be a vectorial sum of the first vector $C_{1st-measured}$ and the speculum induced vector $C_{speculum-induced}$.

Figure 7:
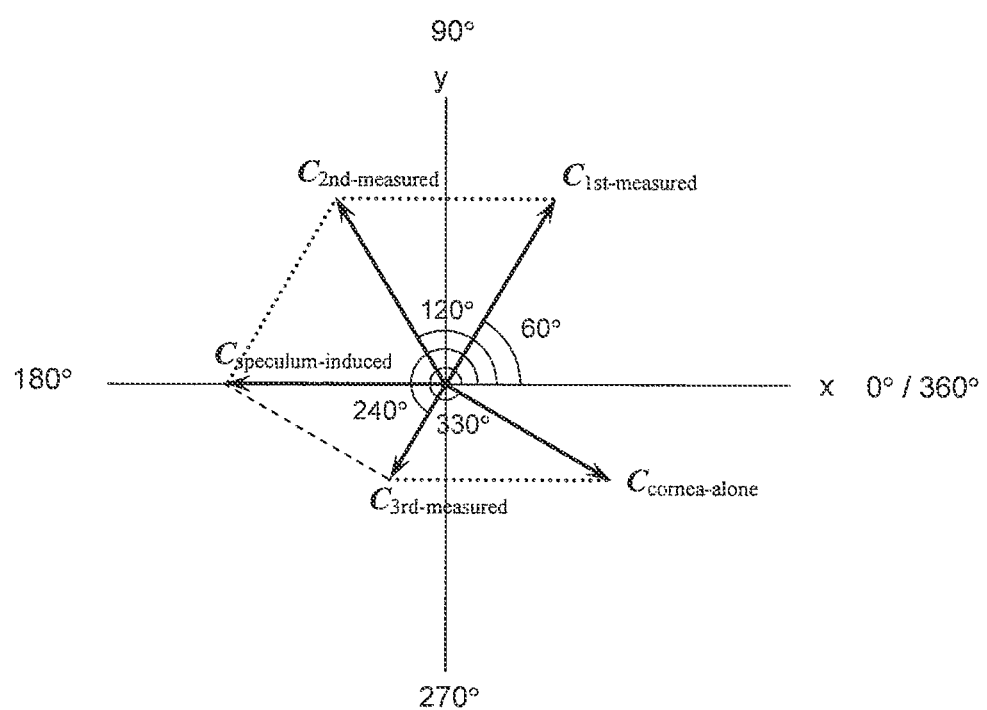
FIG. 7 shows an example of using the double-angle vector diagram to find the astigmatic component induced by the speculum and the astigmatic component of the cornea alone.

As shown in FIG. 7, since the first vector $C_{1st-measured}$ and the second vector $C_{2nd-measured}$ has the same magnitude or vector length and the relative angel between these two vectors is 60°, using either vector addition/subtraction drawing or trigonometry or calculation based on polar or Cartesian coordinate, it can be found that the speculum induced vector $C_{speculum-induced}$ is a vector with a magnitude of 1.00 diopter and a pointing direction along the negative x-axis direction or with an orientation angle of 180°. When this speculum induced astigmatic component is converted back to the eye space, the orientation angle needs to be halved and hence the speculum induced astigmatism is along the vertical direction of the eye with a magnitude of 1.00 diopter. On the live eye image display, a second reference axis can now be marked in the form of a double arrow headed vertical line (i.e. oriented at 90°) of a different color as the electronically assigned second indicator to inform the surgeon that the application of the speculum has induced an astigmatic component along the vertical direction. Alternatively, an updated indicator showing the actual orientation direction of the real time astigmatic axis of the eye under the temporary influence of the speculum can be displayed and tracked to the live eye image, with some kind of differentiation (such as a different color or line pattern) to inform the surgeon that this real time astigmatic axis has the temporary influence of the speculum. This temporary influence will be substantially gone after the speculum is removed from the eye.

If a third intra-operative measurement is made using a wavefront sensor after the natural crystalline lens of the eye has been removed and viscoelastic liquid has be placed in the capsular bag while the eye is aphakic, and it is found that the aphakic eye under the temporary influence of the speculum as well as the non-temporary influence of cornea incision(s), but without the contribution of the natural crystalline lens has a net astigmatism with a magnitude of 0.50 diopter and a meridian or astigmatic axis angle of 120°, then in the double-angle vector diagram, this third measured net astigmatism vector $C_{3rd\text{-}measured}$ can be drawn as a vector with a magnitude of 0.50 diopter and a pointing angle of 240° (120° doubled is 240°) as shown in FIG. 7. Considering that once the speculum is removed from the eye, the speculum induced temporary astigmatic component will be gone, in order to find the astigmatism caused purely by the cornea alone after the cornea restores its original shape but still under the current influence of non-temporary surgical factors such as cornea incision(s), there is thus a need to subtract the temporary speculum induced astigmatic component from the third measured net astigmatism.

In the double-angle vector diagram as shown in FIG. 7, the astigmatism caused purely by the cornea alone is represented by the vector $C_{cornea\text{-}alone}$, which is the vectorial difference between the vector $C_{3rd\text{-}measured}$ and the vector $C_{speculum\text{-}induced}$. In other words, the temporary speculum induced astigmatism vector $C_{speculum\text{-}induced}$ plus the cornea-alone astigmatism vector $C_{cornea\text{-}alone}$ should result in the third measured astigmatism vector $C_{3rd\text{-}measured}$. Using vector addition/subtraction drawing or trigonometry or vector analysis based on polar or Cartesian coordinates, it can be found that the cornea-alone astigmatism has a magnitude of sqrt($1^2-0.5^2$)=0.866 diopters and a pointing angle of 240°+90°=330°. When this cornea-alone astigmatism vector is converted to the real eye space, the angle needs to be halved so the real astigmatic axis angle of the cornea alone astigmatism is 165° in the eye space. On the live eye display, a reference axis of a different color or line pattern can now be marked or drawn electronically in the form of a double arrow headed line pointing at 165° as the electronically assigned indicator to inform the surgeon that the true astigmatism of the cornea alone (including the effect of both the anterior surface and the posterior surface of the cornea and the non-temporary cornea incision effect, but excluding the temporary speculum induced astigmatic components that would be absent after the surgery) has an astigmatic axis of 165°.

Therefore, if a toric IOL is to be implanted, its astigmatic magnitude can be selected based on this calculated magnitude of the cornea-alone astigmatism in order to completely cancel the astigmatic component of the cornea alone and its axis should be rotated and aligned at 165° with respect to the eye. Meanwhile, the sphere dioptric value of the IOL can also be selected based on the measured sphere dioptric value of the cornea alone. Thus, in this example embodiment, the astigmatism magnitude of the selected toric IOL compensates the true measured total astigmatic contribution of the cornea alone and would thus results in a surgical outcome that is superior to existing techniques, such as keratometry or corneal topography or OCT, that only measure a part of the astigmatic contribution of the cornea. Once the refractive prescription of the IOL (including S+C×Axis) is determined, the axis of the cornea-alone contribution can be presented to the surgeon, especially when the eye is in the pseudo-phakik stage as will be discussed further in FIG. 8.

It is important to note that after the implantation of a toric IOL, when the axis of the toric IOL is aligned to the real time measured astigmatic axis of the eye under operation, the current sphere and cylinder values measured of the eye will not be zero because of influence of temporary surgically induced factors and the selection of the toric IOL that has taken into consideration the removal of temporary surgically induced factors. However, with the temporary surgically induced factors digitally removed in the calculation of current refraction, the current refractive measurement will show close to zero sphere and cylinder in real time when the axis of the toric IOL is aligned with the target axis of astigmatism correction/neutralization.

In one embodiment, the real time refraction result of the eye under operation at the pseudo-phakic stage can be that of the eye with the presence of speculum effect or that of the eye with the absence of the speculum effect, depending on if the speculum effect is digitally removed or not for the refractive calculation. In other words, if the real time refraction result of the eye at the pseudo-phakic stage is with the digital removal of the speculum effect, then without the physical removal of the speculum, the real time refraction should approach emmetropia (if this is the target refraction) when the toric IOL is rotated and aligned with the marked target axis. On the other hand, if the real time refraction result of the eye at the pseudo-phakic stage is without the digital removal of the speculum effect, then before the physical removal of the speculum, the real time refraction will not approach emmetropia (if this is the target refraction) when the toric IOL is rotated and aligned with the marked target axis, but the real time refraction will approach emmetropia after the speculum is physically removed from the eye. Either approaches can be practiced by a surgeon and the surgeon can choose the option to have the speculum effect digitally removed when aligning the toric IOL before the physical removal of the speculum, and then to switch to the real time true refraction of the eye without the digital removal of the speculum effect after the speculum if physically removed from the eye to further experimentally confirm if the eye at the time of surgery completion (that is, without the physical presence of the speculum) is truly emmetropic.

However, it should be noted that the above example is a simplified one for illustrating the principle. There can be more surgical transitions and effects that should be monitored and/or considered to reflect the changes in the optical refractive properties of the eye and the needed refractive corrections. For example, the above mentioned selection of the IOL is based only on the refractive correction referenced to an eye at the aphakic stage with the speculum removed from the eye. We know that as the eye heals, there can be further changes to the refractive properties of the eye. Therefore, the effect or influence of surgeon-specific surgically induced factors that affect the astigmatic property change of a patient eye can also be taken into consideration to calculate the target axis of astigmatism neutralization/correction. This is because the habit of a particular surgeon in performing the refractive surgery such as cutting the cornea and sealing the wound can induce certain remnant astigmatism to a post-operative eye during the wound healing process. In this respect, a measurement of the cornea shape and/or the refractive errors of an aphakic eye and/or a pseudo-phakic eye right after the surgery can be collected and compared with a measurement of the cornea shape and/or the refractive errors of a post-operative eye that has completely healed after weeks or months of recovery. A database can be established to find out an average of the cornea shape or eye property change and the associated remnant astigmatism (and sphere) among a certain racial group of patients and such data can therefore be used to create a nomagram and to further improve the calculation of the target axis of astigmatism neutralization/correction. So the same principle can be extended to also consider the effect of eye wound healing such that the selection of the IOL can be referenced to a wound healed eye to even further improve the correction/neutralization of any sphere and astigmatism of a wound healed eye. This would results in a surgical outcome that is even more superior to existing techniques, as will be discussed later.

In the example associated with FIG. 7, the dioptric value and the eye space astigmatic axis orientation angle of the measured or calculated astigmatic components and/or the sphere dioptric value of the corneal alone and/or the prescription of the IOL that should be selected can be displayed to the surgeon quantitatively or qualitatively in the form of numbers, lines, ellipse, circles or other shapes in addition to the electronically marked indicators or reference axes.

It should be noted that the update of the reference axis is an important feature associated with the example embodiments. This is because by measuring the eye optical property before and after each influence of surgical factors and taking into consideration the change in the astigmatic property of the eye at different surgical stages, the accuracy and precision of the target axis for post-operative astigmatism correction and neutralization can be substantially improved.

Note that the indicator(s) can be associated with eye optical property measurement data that are continuously being updated and overlaid on the live eye image. In addition, the indicator(s) can also be overlaid onto a static eye image captured pre-operatively or intra-operatively. A real time wavefront measurement derived identification of the astigmatic axis of the eye or the reference axis for astigmatism correction/neutralization can be selected as the custom reference point(s) and the mark(s) is (are) automatically "drawn" and placed to align with, adjacent to, or referenced to this axis.

Figure 8:
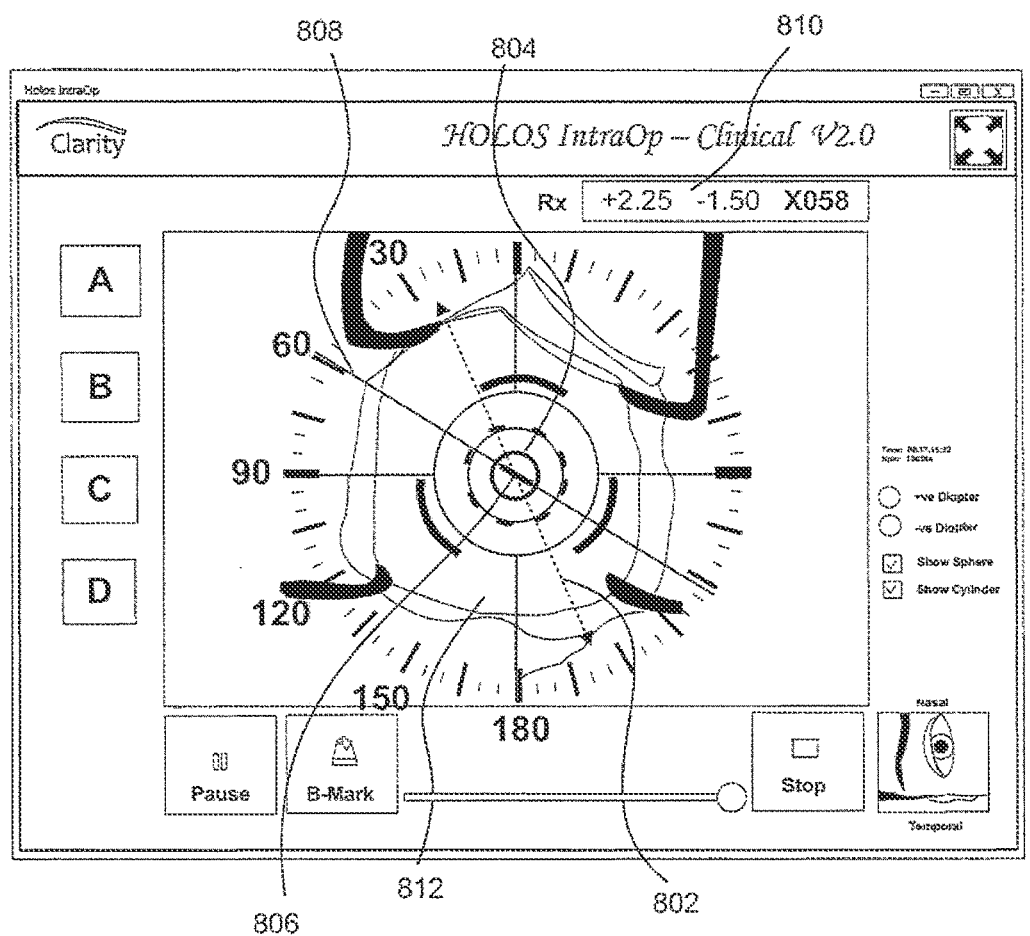
FIG. 8 is a schematic diagram depicting displayed eye image and markings.

FIG. 8 shows an example image of a patient eye with one electronically assigned marking or reference axis as well as the result of real time refractive measurement of the eye. Note that the eye lash is on the left so the horizontal line of eye is vertical in FIG. 8. The double-arrowed long dashed straight line 802 represents the reference axis (an electronically assigned indicator) that overlays a live eye image 812. Meanwhile, real time refraction measurement result is also shown both qualitatively and quantitatively. In one embodiment, the complete circle 804 in the center of the display shows the "sphere" or spherical refractive error of a real time eye refraction measurement where the diameter of the circle represents the "sphere" dioptric value and the color represent sign (positive or negative). The short thicker straight bar 806 in the center of the display shows the "cylinder" or cylindrical refractive error of a real time eye refraction measurement where the length of the straight bar represents the "cylinder" dioptric value and the color represent the sign (positive or negative). The long thin solid straight line 808 drawn along the short thicker straight bar 806 shows the current astigmatic axis from the real time eye refraction measurement. Meanwhile, real time refraction 810 of the eye is also shown quantitatively around the right upper corner of the display in the form of Rx: S+C×Axis, where S refers to the "sphere" dioptric value, C refers to the astigmatism or cylinder dioptric value, and Axis refers to the astigmatic axis angle of the eye in the eye space. Rx denotes the prescription or correction required to neutralize the current real time refractive errors. Note that in this particular example, the long double-arrowed dashed line 802 is the electronically assigned marker corresponding to the axis of astigmatism of the cornea alone without the influence of temporary surgical factors. In other words, the long double-arrowed dashed line 802 is calculated from an aphakic eye refractive measurement but with the deformation of the cornea induced by temporary surgical factors already digitally removed. The solid long thin line 808 is the real time astigmatic axis of a pseudo-phakic eye with a toric IOL implanted but yet to be rotated to the right orientation.

In another embodiment, the reference axis and the real time refraction displayed on the live eye image display reflects not only the current refractive state of the eye with the influence of temporary surgically induced factors, but rather the real time refractive state of the current eye referenced to a wound healed eye with the removal of the influence of temporary as well as surgeon induced factors (i.e. including non-temporary and wound-healing induced factors). For example, the electronically marked reference axis being tracked to live eye movement can be the astigmatic axis of the cornea with the subtraction of astigmatic components induced from all temporary surgically induced factors up to the aphakic stage as well as from surgeon-specific surgically induced factors (including non-temporary and wound healing) due to the surgical habit of an individual surgeon as can be determined from statistical data, whereas the real time refractive errors being displayed are those of a real eye at the pseudo-phakic stage with the implantation of a toric IOL but with the removal of refractive components induced from all temporary surgically induced factors up to the aphakic stage as well as from the surgeon-specific surgically induced factors (including non-temporary and wound healing) due to the surgical habit of an individual surgeon.

In other words, the real time wavefront measurement result at the pseudo-phakic stage of the eye under operation is processed such that what is displayed in real time on the live eye image display is a real time refraction referenced to the relaxed state of the same eye but is post-operative with the wound already healed. In this way, the surgeon selects the astigmatic value of the toric IOL (as well as the sphere dioptric value) and rotates the implanted toric IOL to align it with the electronically marked reference axis. If the centration and effect lens position is correct, this real time refraction referenced to the virtual post-operative eye should approach that of an emmetropic eye or a targeted refraction as determined by the surgeon. Therefore, at this pseudo-phakic stage, the surgeon can compare the dotted axis mark on the implanted toric IOL and align it with the electronically marked reference axis on the live eye image, and/or watch the real time eye refraction until the values approach zero or a targeted refraction.

In an example embodiment, the eye images captured by the camera and the overlaid registration mark(s) are recorded for future playback and analysis. In other embodiment, the registration marks are overlaid on a previously recorded eye image.

The above embodiments allow a surgeon to create reference mark(s) throughout the surgery. For example, the mark(s) can be placed to provide references/registrations describing the state of the patient/eye at the beginning of surgery. For example, the cylinder or astigmatic axis can be measured prior to the beginning of surgery at a phakic stage, and can then be measured intra-operatively at the aphakic and the pseudo-phakic stages. These different measurements allow the surgeon to determine the tempo/change of the magnitude and axis of astigmatism throughout the surgery due to patient's corneal cylinder contribution with and without the lenses (crystalline and IOL) and due to the effect of the corneal incision and use of the eye lid opening speculum. Additionally, the sphere power, corneal shape, eye/axial length, or anterior chamber depth marks and/or values can be referenced/marked in real time as they vary during surgery. The surgeon can use the information to improve the surgical outcome while performing the surgery. For example, if reference marks are made before and after an incision the surgeon receives direct feedback on the refractive effect of the type of decision or procedure made. The surgeon may decide to use a different technique if it is desired to reduce the refractive effects.

The marking can be effected through a "touch" of a button that correlates to the qualitative and/or quantitative data of the eye property measurement (such as aberrometry/auto-refraction); dragged and dropped by the user (surgeon or nurse) via a touch screen or mouse where the user touches the screen; or through audio control, or automatically registered to the patient's canthus, for examples.

Figure 9:
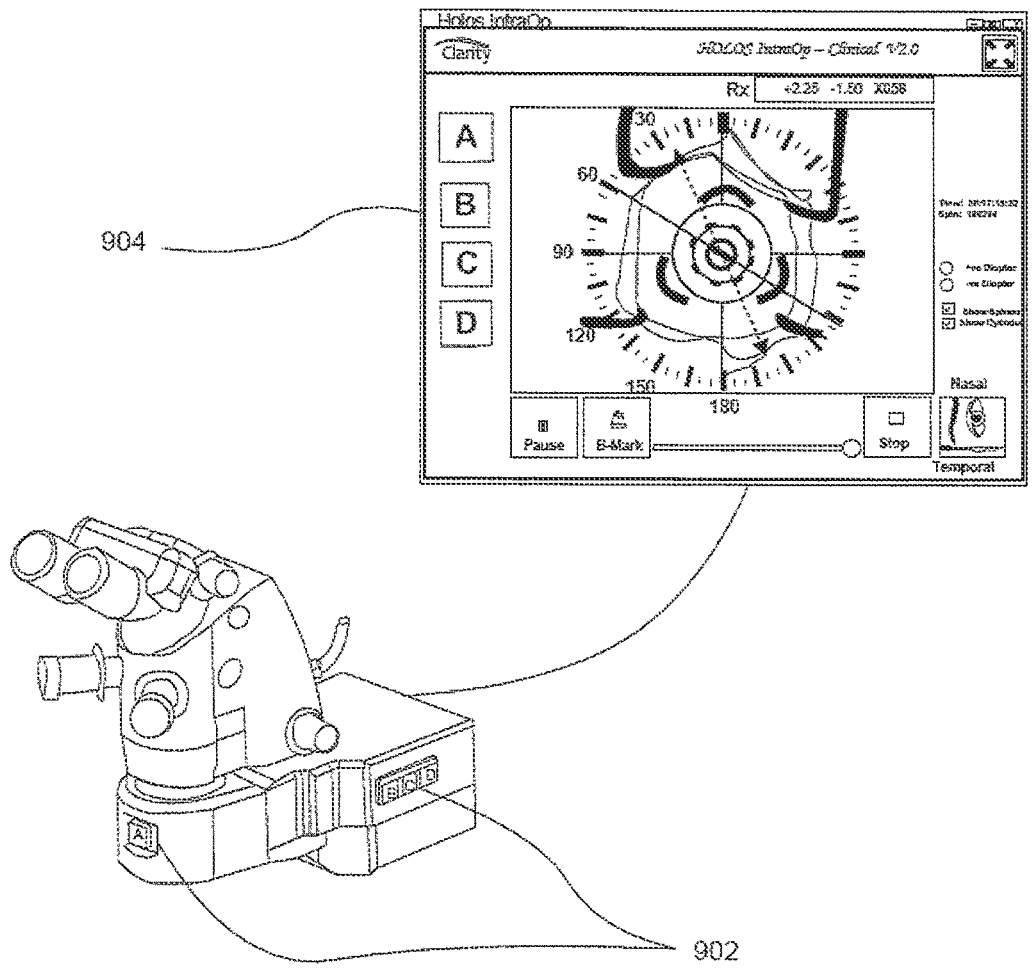
FIG. 9 shows a perspective view of the presently disclosed apparatus integrated or attached to a surgical microscope and electronically linked to a touch screen, with hardware based touch buttons located on the enclosure front and side walls of the apparatus as well as corresponding software based touch buttons on the touch screen.

FIG. 9 is a diagram showing both a perspective view of an example embodiment integrated or attached to a surgical microscope and a touch screen electrically linked to the presently disclosed apparatus. There are hardware based touch buttons A, B, C, and D (902) located on the front and side walls of the apparatus enclosure and/or also corresponding software based touch buttons A, B, C, and D (904) on the touch screen monitor. The hardware buttons can be pressed by the surgeon during surgery to effect the marking or other functions. For example, button A can be used to effect manual marking and/or disable automatic marking; button B can be used to turn on or turn off an internal fixation light; button C can be used as a book mark activation button to highlight certain frame(s) of the recorded eye image; and button D can be used to turn on/off or cycle the output of near infrared flood illumination to better control the brightness and contrast of the live eye image being captured and displayed. There may be other functions not listed here that can be assigned to these buttons.

Although automatic electronic marking can be effected by a built-in algorithm, the surgeon can override the algorithm by pressing the hardware button(s) to select his/her preferred measurement result for the electronic marking and also disable the real time updating of the marking if he/she prefers. This is sometime needed as a subjective judgment made by the surgeon can be better and more reliable because even when the eye is well aligned, the measurement can be influenced by other factors not easily recognizable by the built-in algorithm, including the remaining of irrigation liquid on the cornea of the patient eye, the existence of optical bubbles or debris in the patient eye bag, and insufficient filling of the eye bag with viscoelastic liquid that may cause the intra-ocular pressure of the eye to be outside a normal range. The software based button(s) can be pressed by a nurse during surgery to effect the marking or perform other functions. The same function can also be performed by a nurse using a computer mouse to click the software button(s) or using a computer keyboard. The surgeon can also give voice instruction to the nurse to use the mouse or the keyboard to effect the marking Multiple markings can be effected at different stages as the surgery is on going. Additionally, the surgeon and/or nurse can turn on or off the algorithm used to correct for surgically induced aberrations, wound healing, or other metrics used.

A technique of measurement of cornea contribution to the axis and power of astigmatism is to intra-operatively take wavefront measurements of the aphakic eye to directly measure the cornea contribution. This measurement also has errors because the cornea can be deformed during surgery due to pressure on the eye that distorts the natural "football" shape of the cornea into a different distorted "football" shape. This distortion can be induced by temporary surgical factors such as the application of speculum to hold open the eye lid or the application of irrigation fluid during surgery as well as non-temporary surgical factors such as the incision of the cornea and the healing of surgical wounds. Thus, an intra-operative aphakic measurement characterizes a "distorted football" which will mostly return to its original pre-operative state when the pressure is removed, the eye relaxes and the incision wound has healed. If the toric IOL is rotated based on the aphakic measurement alone without considering all the other factors, then it may not be correctly positioned to cancel the astigmatism of a relaxed and healed eye.

In one embodiment of this disclosure, the electronic marking is a reference axis for better astigmatism correction/neutralization that is calculated through data processing considering these surgical factor(s). For example, there is at least a first measurement of the optical refractive property of an eye taken without any significant influence of surgical factors and there is at least a second measurement of the optical property of the same eye but with the influence of at least one surgical factor (such as the application of the eye lid opening speculum). In this example, the first and second measurements are processed to reveal the change in the astigmatic property of eye, especially during the transition of surgical stages. The measurement may include keratometry measurements, corneal topography measurements, OCT measurements, auto-refraction measurements, aberrometry measurements and/or wavefront measurements. In this example, the second measurement with the influence of surgical factor(s) is made using a real time intra-operative ophthalmic eye optical property measurement device or a combination of two or more devices and examples of such a device include a real time intra-operative keratometer, corneal topographer, optical coherence topographer/tomographer (OCT), auto-refractor, aberrometer, and wavefront sensor.

The purpose of having at least two measurements is to determine any significant change in the astigmatic property (as well as spherical refraction property) of the eye with and without the influence of one or more surgical factor(s) so that an associated change in the target astigmatism neutralization/correction axis for a post-operative eye can be understood, observed, and/or calculated.

It should be re-pointed out here that the two measurements can also include one pre-operative measurement with the patient sitting upright. Therefore, one example embodiment also uses the intra-operative measurement(s) to either confirm the pre-operative measurements performed with varying measurement devices and techniques that are typically used with the patient upright or identify changes in the optical property of the eye. This comparison with the patent sitting up-right versus lying supine could further assist the surgeon in improving patient outcomes.

Figure 10:
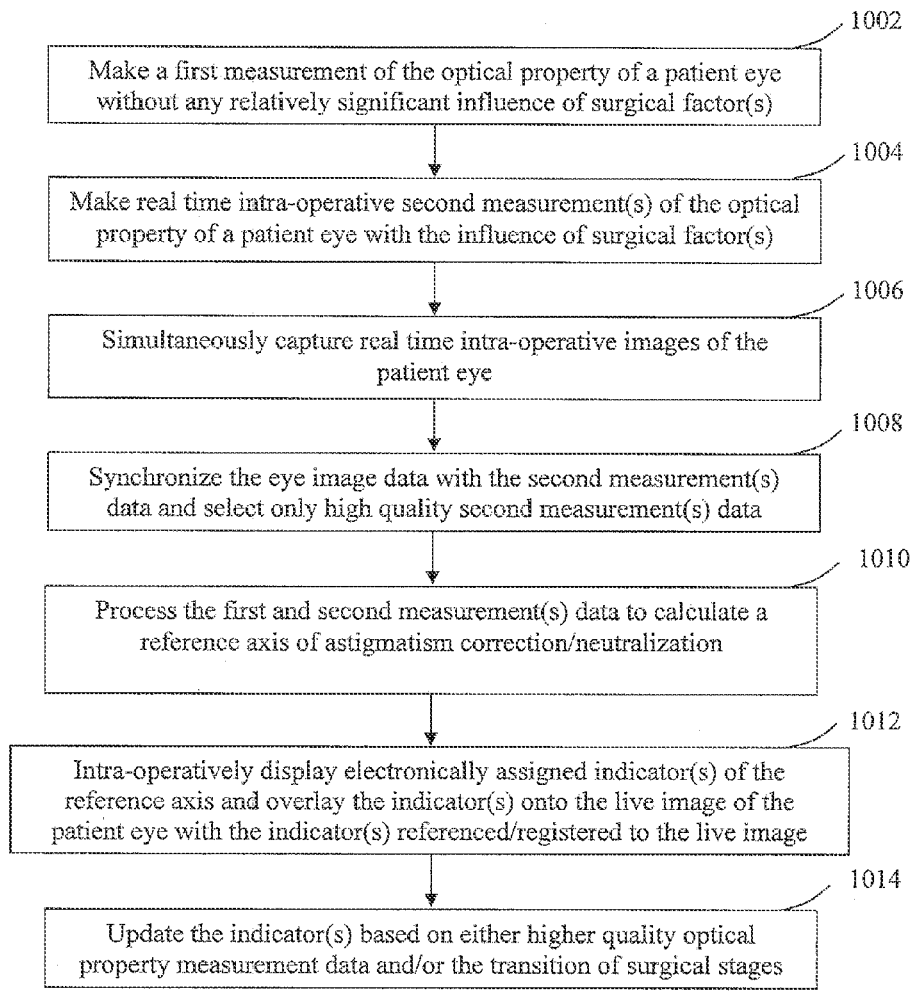
FIG. 10 illustrates one example method for calculating and marking/registering the astigmatism correction/neutralization axis of a patient eye during a refractive surgery.

FIG. 10 illustrates one example method for electronically marking an improved astigmatism correction/neutralization axis during a refractive surgery. At step 1002, a first measurement of the property of a patient eye is made without any significant influence of surgical factor(s). This first measurement can be a keratometry, corneal topography, OCT, auto-refraction, aberrometry or wavefront sensing measurement or a combination of two or more of these measurements. The first measurement can be either a pre-operative one with the patient sitting up-right or an intra-operative one with the patient lying supine.

The purpose of making the first measurement is to record at least one astigmatism related property of the eye at its relatively natural or relaxed state. It should be noted that this natural or relaxed state should be interpreted broadly as an eye with a relatively non-significant or negligible change to the pre-surgical astigmatic property of the eye. A good example is a patient eye with the patient lying supine but before a pair of eye lid opening speculum is applied. In this state, the application of topical anesthesia drops to the eye might have been done but the influence of this surgical factor might be considered negligible. The property of an eye at this state will be relatively similar to that of a natural daily life eye when the patient is in an upright position and it is expected that the difference in the astigmatic property between these two states (upright versus supine) of the same eye is relatively small.

At step 1004, one or more second measurement(s) of the property of a patient eye with the influence of surgical factor(s) is (are) made. This one or more second measurement(s) is (are) made real time intra-operatively and can again be a keratometry, corneal topography, OCT, auto-refraction, aberrometry or wavefront sensing measurement or a combination of two or more of these measurements. The purpose of the second measurement is to record at least the change in the astigmatic property, but could also include other parameters such as the sphere or anterior chamber depth of the eye as a result of the influence of any surgical factor(s).

The second measurement(s) can be made at the phakic, or aphakic or pseudo-phakic stage, with the possibility of making more measurements at one stage versus making one measurement at some or all the stages. Differences between these measurements could also be useful in determining the appropriate astigmatic and/or sphere corrections for the optimal refractive outcome. One good example is a patient eye with the patient lying supine after a pair of eye lid opening speculum has been applied. Another good example is an aphakic eye with the patient lying supine after the natural crystalline lens is removed and viscoelastic liquid is placed in the capsular bag of the eye. Note that the phakic eye measurement with the patient lying supine after a pair of eye lid opening speculum has been applied can also be combined with the aphakic eye measurement with the patient lying supine after the natural crystalline lens is removed and viscoelastic liquid is placed in the capsular bag of the eye. Alternatively, an aphakic keratometric or corneal topographic measurement can be directly combined with an aphakic refraction or wavefront measurement. The aphakic keratometric or corneal topographic measurement will provide information on the change in the cornea shape with the influence of surgical factors and the aphakic refraction or wavefront measurement will provide information on the astigmatism (as well as sphere) of the cornea alone without the contribution from the crystalline lens but with the influence of surgical factors up to this moment. In these cases, several second measurements are made. While a refractive surgery is on-going any real time change in the astigmatic property of the eye can be updated.

It should be noted that the change in the axis and magnitude of the astigmatism of the cornea and/or the eye can potentially occur before, during, and after the refractive surgery so astigmatic property changes can occur at many stages. Examples include from when the eye is phakic and the patient is setting upright to when the patient is lying down in a supine position; from before any iris dilation drop(s) and/or any topical anesthesia drop(s) is (are) applied to the eye to after the application, from before an eye lid speculum is applied to after the speculum is applied to keep the eye open, from before any incision is made to the cornea to after the incision(s) is (are) made; from before the anterior chamber aqueous humor or fluid is replaced to after viscoelastic liquid is introduced; from before the natural crystalline lens is removed while the viscoelastic liquid is in place to after the natural crystalline lens is removed while the viscoelastic liquid is placed in the capsular bag; from before a toric intra-ocular lens (IOL) is introduced to after the IOL is introduced; from before a toric IOL is rotated to during or after the toric IOL is rotated; from before the viscoelastic liquid is removed with the toric IOL in place to after the viscoelastic liquid is removed, from before an LRI/CRI is conducted to during the LRI/CRI is being done to after the LRI/CRL is done; and from before all corneal incisions are sealed to after the sealing; from right after the refractive surgery is completed to several weeks or months after all the wounds have completely healed. Therefore, the first and second eye optical property measurements can measure the difference caused by any the about-mentioned changes.

At step 1006, live images of the eye are simultaneously and continuously captured by the eye camera 508 for display and may also be recorded. Again, the live eye image can also be used to determine how well the eye is aligned with the optical axis of the instrument being used for the real-time intra-operative measurements of the optical properties of the eye.

At step 1008, the live eye image frames are synchronized with the real time eye property measurement data and the quality of the eye property measurement results are determined based on the synchronized eye image data and/or the eye optical property measurement data. A measurement data quality judgement criterion can be established to ensure that only high quality eye property measurement data associated with well-aligned eye images are selected for follow-up data processing. The criterion can be established based on the transverse position of the eye relative to the eye property measurement device, the axial distance of the eye relative to the eye property measurement device, and the optical signal strength from the patient eye. The signal strength will be outside a desired range if the optical path is blocked by a surgical tool or the surgeon's hand or strong reflection of light into the measurement device from a shiny reflective surface of a surgical tool occurs.

At step 1010, the first measurement data and the selected second measurement(s) data are processed to factor in the change in the astigmatic (as well as spherical refraction) property of the eye under the influence of surgical factor(s) and to calculate the axis of astigmatism neutralization/correction. This calculation uses the information of the change in the astigmatic property of the eye to determine the axis of astigmatism neutralization/correction which likely is not the axis of the apparent astigmatism of the eye measured with the influence of current surgical factor(s).

At step 1012, the axis of astigmatism neutralization/correction is electronically marked. The indicator(s) (lines, arrows) associated with the calculated axis of astigmatism neutralization/correction is (are) assigned for association to a specific reference on the eye and is (are) displayed and overlaid onto the live eye image. The reference can be any land mark on the iris, speculum, surgically induced fiducial(s), device fiducial(s), canthus and others. Again, the indicator(s) can also be displayed onto the live eye image in the field of view of the surgical microscope with the indicator(s) referenced to the live eye image of the surgical microscope.

At step 1014, the electronically assigned indicator(s) are updated and overlaid onto the live eye images that are continuously being captured and displayed. Again, the electronically assigned indicator(s) can be updated based on if the eye is even better aligned with the real time intra-operative eye optical property measurement device and/or if the data from the measurement(s) are of even higher quality as can be judged by a built-in data processing algorithm(s) or by a subjective determination from the surgeon. Also, the update can and will likely be performed at different stages of the surgery with one or more updated electronically assigned indicator(s)/marking(s) being displayed and referenced/tracked to the live eye image as mentioned before.

To further improve the surgical outcome of a cataract refractive surgery, additional non-temporary surgically induced effects (such as wound sealing) and wound healing effects can also be taken into consideration in the determination of the axis of astigmatism neutralization/correction and in the selection of a toric IOL at the aphakic stage. As an example, we can assume that from the aphakic stage to the eye completely recovered stage, in addition to the removal of the temporary surgically induced factors (especially the speculum application and removal effect), the cornea incision wound-sealing-and-healing effect is the main factor that will continue to cause further changes to the astigmatic property (as well as the sphere property) of a patient eye. We can also assume that at the aphakic stage, we have made a measurement of the refractive property of the eye and have determined the cornea alone astigmatism (as well as the cornea alone sphere) with the temporary surgically induced astigmatic (and sphere) component(s) removed as shown in FIG. 7. However, the cornea alone vector $C_{cornea-alone}$ in FIG. 7 includes the influence of at least some non-temporary surgical factors such as the incision(s) made in the cornea but not the sealing and healing of the incision. Therefore, a correction of the cornea-alone astigmatism (as well as the sphere), even with the removal of temporary surgically induced astigmatisms, will not be sufficient to completely cancel any remnant astigmatism (and sphere) that can be further induced during the incision sealing and healing process.

Figure 11:
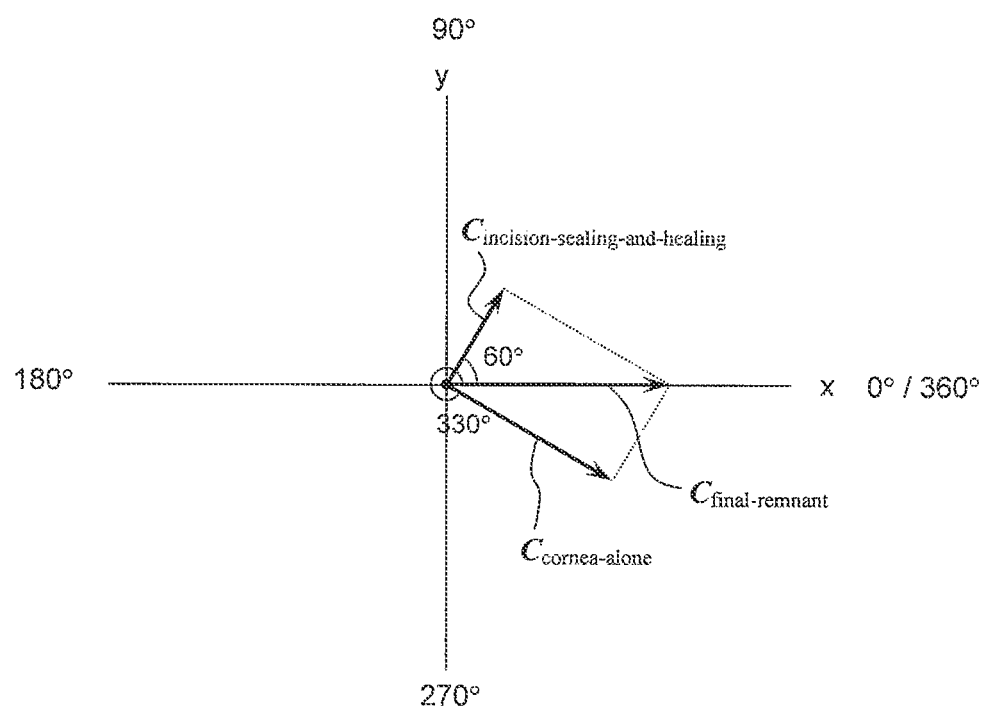
FIG. 11 shows an example embodiment on how to further include the incision-sealing-and-healing effect to further improve the surgical outcome.

FIG. 11 shows an example embodiment on how to further include the incision-sealing-and-healing effect to further improve the surgical outcome. In this double-angle vector diagram, in addition to the cornea alone astigmatism vector $C_{cornea-alone}$, there is also an incision-sealing-and-healing astigmatism vector $C_{incision-sealing-and-healing}$. This vector $C_{incision-sealing-and-healing}$ can be obtained by statistically finding the nominal astigmatism vector difference between the cornea-alone astigmatic component vector and the wound healed astigmatic component vector of a completely recovered eye among a relatively large number of patients of similar racial background from a data base that can be gradually established for a particular individual surgeon.

As shown in FIG. 11, the vectorial summation of the cornea alone astigmatism vector $C_{cornea-alone}$ for the patient currently under surgical operation and the statistical nominal incision-sealing-and-healing astigmatism vector $C_{incision-sealing-and-healing}$ can be considered as the most likely final remnant astigmatism vector $C_{final-remnant}$ that needs to be fully compensated. In this numerical example, in order to make the math simple to illustrate the concept, we have assumed that the statistical nominal incision-sealing-and-healing astigmatism vector $C_{incision-sealing-and-healing}$ has a magnitude of 0.50 diopter and a pointing direction angle of 60° in the double-angle vector diagram (which means that in the eye space, this statistical nominal incision-sealing-and-healing astigmatic component has a magnitude of 0.50 diopter and an astigmatic axis angle of 30°), whereas the cornea alone astigmatism vector $C_{cornea-alone}$ has the same magnitude of 0.866 diopters and a pointing angle of 330° as shown in FIG. 7. Since the relative angle (in the double-angle vector diagram) between the $C_{cornea-alone}$ vector of 0.866 diopter and the $C_{incision-sealing-and-healing}$ vector of 0.50 diopter is 90°, using vector addition/subtraction drawing or trigonometry or vector analysis based on polar or Cartesian coordinates, it can be found that the most likely final remnant astigmatism vector $C_{final-remnant}$ is a vector with a magnitude of sqrt($0.866^2+0.5^2$)=1.00 diopter and a pointing direction angle of 0°. When this most likely final remnant astigmatism is converted to the eye space, it has magnitude of 1.00 diopter and an astigmatic axis of 0° (0° halved is still 0°).

Therefore, to fully compensate this most likely remnant astigmatism (and sphere) of the eye under operation, the toric IOL to be selected at the aphakic stage should have an astigmatism or cylinder component that can cancel or neutralize a 1.00 diopter cylinder and the target axis of astigmatism correction/neutralization should be at 0°, as well as a sphere component that can be determined in a similar way using non-vector but scalar sphere diopter addition and subtraction method. In other words, in this example embodiment, the target axis 802 of the electronic indicator/mark would be oriented at the angle of 0° or along the horizontal direction of the patient eye and the S+C values of the IOL would have magnitudes respectively determined by the scalar sphere addition/subtraction method and by the vector $C_{final-remnant}$.

An improved procedure of surgically implanting a toric IOL will now be described. The purpose of a toric IOL is to compensate and/or correct the astigmatism caused by the non-spherical "football shape" of the cornea in addition to correcting the spherical refractive error. Reference will now be made to the flow chart of FIG. 12, the vector diagram of FIG. 7 and FIG. 11, and the image of FIG. 8. Typically, keratometric measurements of the anterior surface shape of a patient cornea are made prior to surgery and the axis and power of keratometric astigmatism are calculated based on those measurements. A toric IOL has markings that indicate an axis of astigmatism correction to be aligned with the axis of astigmatism correction/neutralization marked on the eye.

In this example, we assume that a keratometric measurement has been made prior to surgery. A keratometric measurement is preferred over a wavefront measurement prior to the aphakic stage because a cataract crystalline lens is generally cloudy and can scatter light in unpredictable way that may affect the result of wavefront measurement. We also assume that at the aphakic stage, two intra-operative measurements have been made, one being an intra-operative keratometric measurement and the other being an intra-operative refraction or wavefront measurement. We also assume that the data of these two intra-operative measurements and the pre-operative keratometric measurement have been processed to reveal the cornea-alone astigmatism/sphere and statistical nominal incision-sealing-and-healing induced astigmatism and sphere have been factored in to find out the S+C×Axis values of the toric IOL to be selected. Now the dashed axis 802 in FIG. 8 represents the orientation of the astigmatic axis of the most likely final remnant astigmatism of the eye. The corresponding cornea-alone astigmatism vector is depicted as $C_{cornea-alone}$ in FIG. 7 and FIG. 11 and the corresponding most likely final remnant astigmatism vector is depicted as $C_{final-remnant}$ in FIG. 11. The cornea-alone S+C×Axis values and the most likely final remnant S+C×Axis values are not displayed in FIG. 8, but either or both can be displayed if needed.

In this example embodiment, the IOL prescription in terms of the S+C×Axis values of a toric IOL is not displayed in FIG. 8 (but can be displayed if desired) and the S+C×Axis values shown at the upper right corner of the display in FIG. 8 are the real time refractive measurement result of the eye under operation with the digital removal of astigmatism and sphere components induced by both temporary and surgeon specific surgical factor(s) that would be gone after the eye has completely recovered several weeks or months later.

Figure 12:
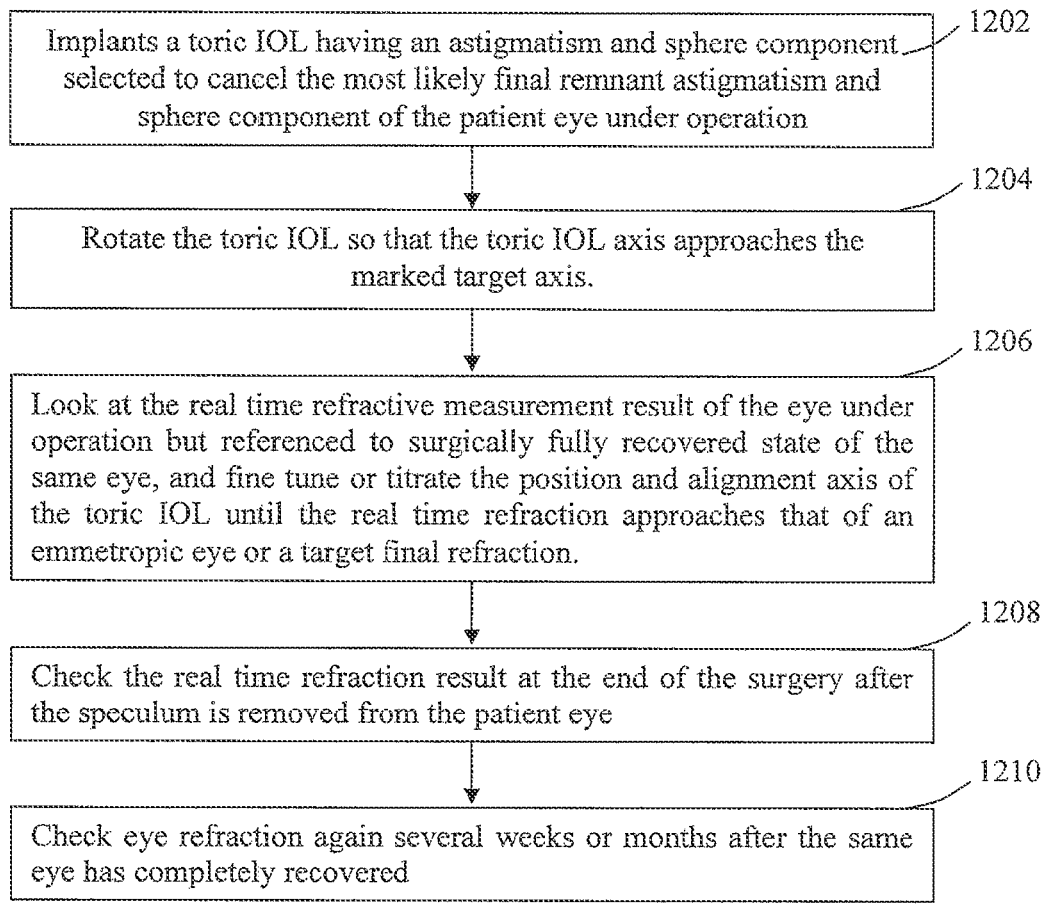
FIG. 12 shows an example flow chart of an improved procedure of surgically implanting a toric IOL.

FIG. 12 shows an example flow chart of an improved procedure of surgically implanting a toric IOL. In process step 1202 the surgeon implants a toric IOL having an astigmatism and sphere component selected to cancel the most likely final remnant astigmatism and sphere component of the patient eye under operation. Generally, a toric IOL is designed to be easily rotated in one direction, in this example clockwise direction. The surgeon generally implants the toric IOL with the axis in a certain position some degrees counter-clockwise from the target axis so that the surgeon will then rotate the toric IOL to the target axis.

During surgery, in process step 1204 the surgeon rotates the toric IOL so that the toric IOL axis approaches and aligns with the marked target axis 802.

When the two axes are aligned the real time S+C values (810) as displayed in the window of FIG. 8 will approach zero if the targeted post-operative eye is emmetropic. As an optional step, in process step 1206, the surgeon also looks at the real time refractive measurement result of the eye under operation but referenced to surgically fully recovered state of the same eye, and fine tune or titrate the position and axis of the toric IOL until the real time refraction approaches that of an emmetropic eye or a target final refraction.

As another alternative, in process step 1208, the surgeon can also check the real time refraction result at the end of the surgery after the speculum is removed from the patient eye. In this case, the surgeon can have the option to switch the real time refraction measurement result from the speculum-present-display-format (i.e. with temporary surgically induced factors digitally removed from the measurement result) to the speculum-absent-display-format (i.e. without the digital removal of temporary surgically induced factors since the speculum is removed already). This switch will provide better experimental confirmation on the accuracy and precision of the digital removal of the temporary surgical factors. The experimental confirmation can also serve as a data point for increasing the established data base to further improve the statistics of the wound healing induced refractive changes of similar eyes.

As still another alternative, in process step 1210, the surgeon can check eye refraction again several weeks or months after the same eye has completely recovered and this time, the influence of wound healing effect should be digitally removed from the calculation so that the wavefront sensor is measuring exactly the real time refraction of the same eye. This can serve as a final experimental verification or confirmation and the measurement result can even be compared with a subjective phoropter test result to further improve the end point data accuracy and precision of the established data base.

One unique feature of the example embodiments is the intra-operative calculation, at the aphakic stage, of the refractive error of the cornea alone with the removal of those refractive errors induced by temporary surgical factors that would no longer be present once the surgical factors are removed as well as the consideration of surgeon induced refractive errors that would be induced as the operated eye is recovers. In doing so, an optimized intra-ocular lens (IOL), especially a toric IOL, can be selected at the aphakic stage, and also later intra-operatively confirmed at the pseudo-phakic stage when the IOL is properly positioned, especially when the toric IOL is properly rotated and aligned, as well as when the speculum is finally removed from the eye.

Another unique feature of the example embodiments is the display of real time refraction of an eye under operation but referenced to a post surgery eye (i.e. with the digital removal of temporary surgical factors) and a post-operative wound-healed state of the same eye (i.e. with the removal of both temporary and surgeon induced factors). With this approach, all surgical factors that could have induced extra refractive changes to the eye and would be gone either right after the surgery or weeks or months after the surgery, including individual surgeon induced remnant refractive errors, are removed for the calculation of the real time refraction. Therefore, at the pseudo-phakic stage when the surgeon is either rotating an implanted toric IOL to fine tune its alignment angle or performing a LRI or CRI, if the "final touch" is in the correct direction, the real time refraction referenced to the virtual post surgery eye or a post-operative wound-healed state of the same eye should approach that of an emmetropic eye or a targeted refraction as determined by the surgeon.

It should be noted that there can be different variation of the details in terms of the eye property measurements, live eye image capturing/recording and display, high quality measurement data selection, data processing to identify the astigmatic axis or the axis of astigmatism correction/neutralization of an eye under refractive surgery, and electronic marking/registration. For example, the eye property measurement device does not need to be restricted or limited to an auto-refractor or an aberrometer or a wavefront sensor or a keratometer or a corneal topographer or an optical coherence topographer/tomographer. The measurement device can even be a retina/fundus camera that can directly capture a retinal image of a point light source and hence directly find the point spread function of the eye, which can then be used to characterize the astigmatic and/or refractive and/or aberration property of the eye.

The live eye image capturing device does not need to be restricted to a near infrared camera. It can be a camera operating in the visible or other wavelength range. It can be a slit-lamp bio-microscope for example. It can also be a separate camera that can be attached to the eye piece of the auxiliary viewing port of a surgical microscope. The image does not need to be limited to the anterior of the eye. In addition to the iris of the eye, any eye portion that contains reference land marks can be used, as the live image is used to judge the alignment of the eye relative to the eye optical property measurement device and also to track the eye. In this respect, the live eye image can be the white of the eye, the canthus of the eye, the eye lashes, surgically/surgeon placed fiducial(s), the eye lid opening speculum, or even the head of the patient.

The synchronization of the eye optical property measurement data with live eye image frames can be achieved using any data processor, including a dedicated chip processor and a computer. The identification and selection of relatively high quality eye property measurement data can be achieved in real time automatically using a built-in algorithm or program without or with additional alignment detection means. However, the identification and selection can also be done non-real-time using a separate data processor or even manually by a surgeon or a nurse. The captured live eye images and the eye optical property measurement results can be digitally recorded and played-back in the OR (operating room) such that the surgeon can subjectively select those measurement data that he/she believes are of high quality when the eye is/was well aligned with the eye property measurement device and there is no other interference such as the irrigation of the eye.

The synchronized data collected and recorded, can be viewed during playback for the surgeon to review the surgical case steps/process, the causal relationships of surgical techniques, and other influences. These recordings can be used by the surgeon to improve the surgeon's techniques and procedures, collect data for improving the surgeon's nomograms, or for training purposes etc.

The calculation of the astigmatic axis of the eye or the axis of astigmatism correction/neutralization can be performed using the same data processor that does the job of high quality data selection, or using a different processor. In the case that there is no reference eye optical property measurement without the influence of surgical factor(s), the astigatic axis of either the anterior surface of the cornea (keratometry or corneal topography), or the whole cornea (aphakic eye refraction measured by an auto-refractor or a wavefront sensor) or the whole eye (phakic eye auto-refraction or wavefront measurement) can be directly used as the reference axis for astigmatism correction/neutralization. In the case that there is a first reference eye optical property measurement without any significant influence of surgical factor(s), the first measurement can be compared with (a) second measurement(s). The first reference measurement can be a pre-operative one (such as a pre-operative keratometry measurement or a pre-operative wavefront measurement) or an intra-operative one (such as a keratometry or wavefront measurement before the application of eye lid opening speculum). A comparison between the first reference measurement and (a) second measurement(s) can be used to find out if there is any change in the astigmatic (as well as refractive) property of the eye as a result of the influence of surgical factor(s) (such as the application of the speculum). If there is no or negligible change, the result of the second measurement(s) can directly be used to find the reference axis. If there is a significant change, this indicates that the astigmatic axis as measured by the second measurement(s) cannot be directly used as the reference axis. But the change can be used for a calculation to find out the target axis of astigmatism correction/neutralization. Note that there can be more than one type of second measurements and that the more than one type of second measurements can be combined.

Two very useful second measurements are an eye optical refractive property measurement after the application of a pair of eye lid opening speculum and an aphakic auto-refraction or wavefront measurement. The second measurement after the application of a pair of eye lid opening speculum can be made either at the phakic or the aphakic stage and be compared to a first reference measurement made before the application of a pair of eye lid opening speculum to find out the change in the cornea shape or eye optics as a result of speculum application. The difference between the measured "football" shape of the cornea before the application of surgical factors and the measured "football" shape after the application of the surgical factors can be used to calculate the induced change in the axis and power of the astigmatism (as well as the overall refraction) of the eye) due to the application of surgical factors.

The aphakic auto-refraction or wavefront measurement can directly reveal the astigmatism of an aphakic eye (with the cornea but without the natural crystalline lens). However, the accuracy of this measurement can be affected by the distortion of the cornea induced by the applied surgical factors. The accuracy and precision of the reference axis can be improved by factoring in the change in the cornea shape and assuming that the cornea will regain its original shape. The accuracy and precision of the reference axis can be even further improved by factoring in the change in the refraction of the eye induced during the wound healing process. The induced changes in astigmatism (as well as over refraction that include sphere) can be factored into the measured aphakic astigmatism to calculate the target axis of astigmatism correction/neutralization for intra-operative toric IOL rotation and the selection of the toric IOL as well as other surgical procedures such as the position to conduct an LRI or CRI. This target axis, which is different from the measured aphakic astigmatic axis, will give the surgeon a better reference than the aphakic astigmatic axis in terms of canceling the eye astigmatism after the cornea regains its original shape and after the eye has completely recovered from the surgery.

It should also be noted that the second measurement(s) does (do) not have to be limited to concurrent measurement(s) as the surgeon can pause the surgery momentarily, and manually as well as subjectively select one or more high quality second measurement(s) to give him/her the reference axis and then continue the surgery. One reason for a subjective selection of high quality eye optical property measurement data is that there can be surgical factors that can influence the astigmatic property of the eye but are not easily detectable by a built-in algorithm. Examples of such factors include the irrigation of the eye, the incomplete removal of any remaining lens or cortex debris in the eye bag or the existence of optical bubbles in the eye. These can be better identified by the surgeon, so sometimes subjective selection can lead to better results. Note also that the second measurement(s) data can also be those obtained across a group of patients and statistically analyzed. One example is surgeon induced remnant astigmatism that is specific to an individual surgeon.

The electronic assignment of indicator(s) of the astigmatic axis or the target axis, or predictive axis of astigmatism correction/neutralization and the registration of the indicator(s) with a live eye image can be performed by the same data processor or a different processor. The display can be that of the surgical microscope or a separate display/monitor or a heads-up display or a built-in semi-transparent display inside one or both of the binoculars of the surgical microscope. The electronic marking/registration can be in the format of an angular measurement dial or reticle with angular graduations and a straight line showing the astigmatic axis or the target axis of astigmatism correction/neutralization. But the marking/registration can also be in other formats such as in the form of an arrow showing the astigmatic axis. The marking/registration of the astigmatic axis or the target axis of astigmatism correction/neutralization can also be highlighted tick mark around the dial or reticle having angular graduations.

It should also be noted that although we have used refractive errors or refractive power for most of the discussion so far. The concept can be directly extended to include both lower order and high order aberrations of the eye. In other words, the result of eye optical property measurements can include not only the second order aberration of either the cornea anterior surface and/or the whole but also the third, fourth, and other higher order aberrations of the cornea anterior surface and/or the whole eye. Accordingly, in addition to the second order aberrations which include defocus and astigmatism (i.e. sphere and cylinder), the discussions can be applied to all other order aberration components.

The various embodiments described can be applied to any real time vision correction procedure in addition to refractive surgeries such as cataract surgery, LASIK, PRK, LRI/CRI, Femto-second. The example embodiments can also be applied to any real time wavefront correction device that may also have interactive factors affecting the real time wavefront.

Although various embodiments that incorporate the teachings of the present invention have been shown and described in detail herein, those skilled in the art can readily devise many other varied embodiments that still incorporate these teachings.

What is claimed is:

1. An apparatus for measuring astigmatic components of a patient eye during a cataract refractive surgery, comprising:
a real-time intra-operative wavefront sensor configured to continually sample a first set of wavefronts returned from a patient eye during a first intra-operative time interval, where temporary surgically-induced factors that cause temporary changes to a pre-surgery measured astigmatic component of the patient eye occur during the first intra-operative time interval, where the first set of wavefronts is sampled after the removal of a crystalline lens of the patient eye putting the patient eye in an aphakic state, and with the real-time intra-operative wavefront sensor configured to output wavefront measurement data characterizing the first set of wavefronts; and
a data processor, coupled to the real-time intra-operative wavefront sensor to receive the wavefront measurement data, configured to calculate an aphakic astigmatic component from wavefront data characterizing samples of the first set of wavefronts and to calculate a cornea-alone astigmatic component being a difference of the aphakic astigmatic component and a temporary astigmatic component, where the temporary astigmatic component is a measurement of the temporary astigmatic change caused by the temporary surgically-induced factors, and with the data processor further configured to output the cornea-alone astigmatic component.

2. The apparatus of claim 1 with the data processor further configured to:
output the cornea-alone astigmatic component during the refractive surgery.

3. The apparatus of claim 2 further comprising:
a display, coupled to the data processor, configured to display the cornea-alone astigmatic component.

4. The apparatus of claim 1 with the data processor further configured to:
output the cornea-alone astigmatic component during the refractive surgery when the eye is in the aphakic state.

5. The apparatus of claim 1 further comprising:
an intra-operative corneal-shape measurement device configured to output a first phakic corneal shape measurement of the patient eye taken before the first intra-operative time interval and before the crystalline lens is removed and to output a second phakic or aphakic corneal shape measurement of the patient eye taken during the first intra-operative interval; and
with the data processor further coupled to the intra-operative corneal-shape measurement device to receive the first phakic corneal shape measurement and the second phakic or aphakic corneal shape measurement and further configured to calculate the temporary astigmatic component based on the first phakic corneal shape measurement and the second phakic or aphakic corneal shape measurement.

6. The apparatus of claim 5, where the intra-operative corneal-shape measurement device is a keratometer, keratoscope, corneal topographer, or an optical coherence topographer/tomographer.

7. The apparatus of claim 5 further comprising:
a housing configured to be attached to or integrated with a surgical microscope, where the real-time intra-operative wavefront sensor, the data processor and the intra-operative corneal-shape measurement device are disposed within the housing.

8. The apparatus of claim 1 with:
the real-time intra-operative wavefront sensor configured to sample a second and a third set of wavefronts, where the second set of wavefronts is returned from the patient eye before the first intra-operative time interval and before the removal of the crystalline lens when the patient eye is in a phakic state and where the third set of wavefronts is returned from the patient eye during the first intra-operative time interval and with the patient eye in the phakic state, and with the real-time intra-operative wavefront sensor configured to output wavefront measurement data characterizing the second and third sets of wavefronts; and
with the data processor further configured to calculate first and second phakic astigmatic components from the wavefront data characterizing the second and third sets of wavefronts and configured to calculate the difference between the first and second phakic astigmatic components to obtain the temporary astigmatic component.

9. The apparatus of claim 1 with:
the real-time intra-operative wavefront sensor configured to sample a fourth set of wavefronts, where the fourth set of wavefronts is returned from the patient eye during the first intra-operative time interval and is sampled after implantation of an intra-ocular lens when the patient eye is in a pseudo-phakic state and with the real-time intra-operative wavefront sensor configured to output wavefront measurement data characterizing the fourth set of wavefronts; and
with the data processor further configured to calculate a pseudo-phakic astigmatic component from the wavefront data characterizing the fourth set of wavefronts and further configured to output the pseudo-phakic astigmatic component.

10. The apparatus of claim 1 further comprising:
a housing configured to be attached to or integrated with a surgical microscope, where the real-time intra-operative wavefront sensor and the data processor are disposed within the housing.

11. The apparatus of claim 1 with the data processor configured to:
calculate an anticipated post-surgery astigmatic component being the summation of the cornea-alone astigmatic component and a surgeon-induced astigmatic component and to output the anticipated post-surgery astigmatic component during the cataract refractive surgery.

12. An apparatus for displaying intra-operative measurements of a patient eye during cataract refractive surgery, the apparatus comprising:
a real-time intra-operative wavefront sensor configured to continually sample a first set of wavefronts returned from a patient eye during a first intra-operative time interval, where temporary surgically-induced factors that cause temporary changes to a pre-surgery measured astigmatic component of the patient eye occur during the first intra-operative time interval, where the first set of wavefronts is sampled after the removal of a crystalline lens of the patient eye putting the patient eye in an aphakic state, and with the real-time intra-operative wavefront sensor configured to output wavefront measurement data characterizing the first set of wavefronts;

a real-time eye camera configured to output real-time digital images of the patient eye during the cataract refractive surgical procedure; and a data processor, coupled to the real-time intra-operative wavefront sensor to receive the wavefront measurement data and coupled to the real-time eye camera to receive the real-time digital images, configured to calculate an aphakic astigmatic component from wavefront data characterizing samples of the first set of wavefronts and to calculate a cornea-alone astigmatic component being a difference of the aphakic astigmatic component and a temporary astigmatic component, where the temporary astigmatic component is a measurement of the temporary astigmatic change caused by the temporary surgically-induced factors, and with the data processor further configured to output a digital image having the cornea-alone astigmatic component displayed together with the real-time digital image of the patient eye during the refractive surgery.

13. The apparatus of claim 12 further comprising:
a display connected to the data processor and where the cornea-alone astigmatic component includes a cornea-alone axis of astigmatism, with the display configured to display a live eye image of the patient eye and the cornea-alone axis of astigmatism that is tracked to the movement of the live eye image.

14. The apparatus of claim 12 further comprising:
an intra-operative corneal-shape measurement device configured to output a first phakic state corneal shape measurement of the patient eye before the first intra-operative time interval and before the crystalline lens is removed and to output a second phakic or aphakic corneal shape measurement of the patient eye during the first intra-operative interval; and with the data processor further coupled to the intra-operative corneal-shape measurement device to receive the first phakic corneal shape measurement and the second phakic or aphakic corneal shape measurement and further configured to calculate the temporary astigmatic component based on the first phakic corneal shape measurement and the second phakic or aphakic corneal shape measurement.

15. The apparatus of claim 14, where the intra-operative corneal-shape measurement device is a keratometer, keratoscope, corneal topographer, or an optical coherence topographer/tomographer.

16. The apparatus of claim 14 further comprising:
a housing configured to be attached to or integrated with a surgical microscope, where the real-time intra-operative wavefront sensor, the intra-operative corneal-shape measurement device, the real-time eye camera and the data processor are disposed within the housing.

17. The apparatus of claim 12 with:
the real-time intra-operative wavefront sensor configured to sample a second and a third set of wavefronts, where the second set of wavefronts is returned from the patient eye before the first intra-operative time interval and before the removal of the crystalline lens when the patient eye is in a phakic state and where the third set of wavefronts is returned from the patient eye during the first intra-operative time interval and with the patient eye in the phakic state, and with the real-time intra-operative wavefront sensor configured to output wavefront measurement data characterizing the second and third sets of wavefronts; and with the data processor further configured to calculate first and second phakic astigmatic components from the wavefront data characterizing the second and third sets of wavefronts and configured to calculate the difference between the first and second phakic astigmatic components to obtain the temporary astigmatic component.

18. The apparatus of claim 12 with:
the real-time intra-operative wavefront sensor configured to sample a fourth set of wavefronts, where the fourth set of wavefronts is returned from the patient eye during the first intra-operative time interval and is sampled after implantation of an intra-ocular lens when the patient eye is in a pseudo-phakic state and with the real-time intra-operative wavefront sensor configured to output wavefront measurement data characterizing the fourth set of wavefronts;

with the data processor further configured to calculate a pseudo-phakic astigmatic component from the wavefront data characterizing the fourth set of wavefronts and further configured to generate a digital image having both the cornea-alone astigmatic component and the pseudo-phakic astigmatic component displayed together with the real-time digital image of the eye.

19. The apparatus of claim 18 where the cornea-alone astigmatic component includes a cornea-alone axis of astigmatism and where the pseudo-phakic astigmatic component includes a pseudo-phakic axis of astigmatism and with the digital processor further configured to:
output a digital image having both the cornea-alone and the pseudo-phakic axes of astigmatism overlaying the real-time digital image of the eye in real time during the cataract refractive surgery.

20. The apparatus of claim 19 further comprising:
a display connected to the data processor and with the display configured to display a live eye image of the patient eye, the cornea-alone and the pseudo-phakic axes of astigmatism that are tracked to the movement of the live eye image.

21. The apparatus of claim 18 further comprising:
a user input device; and
with the data processor further configured to:
update a reference axis based on user input from a surgeon or nurse.

22. The apparatus of claim 21 further comprising:
a recording device configured to record the digital image having the cornea-alone axis of astigmatism overlaying the real-time digital image of the eye; and
with the processor further configured to:
update a reference axis based on user input from a surgeon or nurse when the surgeon or nurse is viewing a recording of the cornea-alone axis of astigmatism overlaying the real-time digital image of the eye.

23. The apparatus of claim 12 further comprising:
a housing configured to be attached to or integrated with a surgical microscope, where the real-time intra-operative wavefront sensor, the real-time eye camera and the data processor are disposed within the housing.

24. The apparatus of claim 12 with the data processor configured to:
calculate an anticipated post-surgery astigmatic component being the summation of the cornea-alone astigmatic component and a surgeon-induced astigmatic component and to output the anticipated post-surgery astigmatic component in real time.

25. The apparatus of claim 12 with the data processor further configured to:
process real-time digital images of the patient eye to judge the alignment of the eye relative to the real-time intra-operative wavefront sensor.

26. The apparatus of claim 25 with the data processor further configured to:
  calculate a measurement data quality judgment criterion based on the alignment of the eye.

27. The apparatus of claim 12 with the data processor further configured to:
  electronically assign an indicator of a reference axis of astigmatism correction/neutralization for association to a specific reference on the digital eye image and display the indicator onto the live eye images with the indicator referenced to the live eye images; and
  update the indicator based on either higher quality eye property measurement data or a transition of surgical states.

28. The apparatus of claim 27 where the selection of only high quality eye property measurement data is based on a criterion taking into consideration the position of the patient eye relative to the measurement device being used for making the real time intra-operative measurement and the signal strength range of the eye property measurement.

29. The apparatus of claim 12 with the data processor further configured to:
  assign an indicator for astigmatism correction/neutralization during the cataract refractive surgery, with the indicator representing a reference axis or a target axis, where a reference axis is the astigmatic axis of the patient eye at different surgical states and where a target axis is the astigmatic axis of an anticipated post-operative wound-healed patient eye that has taken into consideration the removal of temporary astigmatic component and/or the addition of surgeon-induced astigmatic component.

30. The apparatus of claim 12 with the data processor further configured to:
  output information for comparison with a post-operative eye property measurement after the treated eye has completely healed.

31. The apparatus of claim 12 with the data processor further configured to:
  output information for processing with other information collected before, during and after the refractive surgery to establish a nomogram for calculating a target axis of astigmatism correction/neutralization that also takes into consideration surgery-induced remnant astigmatism specifically associated with an individual surgeon's practice habit.

32. An apparatus comprising:
  a surgical microscope having a front end for collecting light;
  a module coupled to the front end of the surgical microscope, with the module including:
  a real-time intra-operative wavefront sensor configured to continually sample a first set of wavefronts returned from a patient eye during a first intra-operative time interval, where temporary surgically-induced factors that cause temporary changes to a pre-surgery measured astigmatic component of the patient eye occur during the first intra-operative time interval, where the first set of wavefronts is sampled after the removal of a crystalline lens of the patient eye putting the patient eye in an aphakic state, and with the real-time intra-operative wavefront sensor configured to output wavefront measurement data characterizing the first set of wavefronts;
  a real-time eye camera configured to output real-time digital images of the patient eye during a cataract refractive surgical procedure; and
  a data processor, coupled to the real-time intra-operative wavefront sensor to receive the wavefront measurement data and coupled to the real-time eye camera to receive the real-time digital images, configured to calculate an aphakic astigmatic component from wavefront data characterizing samples of the first set of wavefronts, to calculate a cornea-alone astigmatic component being a difference of the aphakic astigmatic component and a temporary astigmatic component, where the temporary astigmatic component is a measurement of the temporary refractive change caused by the temporary surgically induced factors and with the data processor further configured to output a digital image having the cornea-alone astigmatic component displayed together with the real-time digital image of the patient eye in real time during the cataract refractive surgery.

33. The apparatus of claim 32 with the surgical microscope having an optical path and further including:
  a transparent display, disposed in the optical path and coupled to the data processor, for displaying a digital image, output by the data processor, having the cornea-alone astigmatic component overlaying the real-time live microscopic image of the patient eye in real time during the refractive surgery.

34. The apparatus of claim 32 with:
  the real-time intra-operative wavefront sensor configured to sample a second and a third set of wavefronts, where the second set of wavefronts is returned from the patient eye before the first intra-operative time interval and before the removal of the crystalline lens when the patient eye is in a phakic state and where the third set of wavefronts is returned from the patient eye during the first intra-operative time interval and with the patient eye in the phakic state, and with the real-time intra-operative wavefront sensor configured to output wavefront measurement data characterizing the second and third sets of wavefronts; and
  with the data processor further configured to calculate first and second phakic astigmatic components from the wavefront data characterizing the second and third sets of wavefronts and configured to calculate the difference between the first and second phakic astigmatic components to obtain the temporary astigmatic component.

35. The apparatus of claim 32 with:
  the real-time intra-operative wavefront sensor configured to sample a fourth set of wavefronts, where the fourth set of wavefronts is returned from the patient eye during the first intra-operative time interval and is sampled after implantation of an intra-ocular lens when the patient eye is in a pseudo-phakic state and with the real-time intra-operative wavefront sensor configured to output wavefront measurement data characterizing the fourth set of wavefronts; and
  with the data processor further configured to calculate a pseudo-phakic astigmatic component from the wavefront data characterizing the fourth set of wavefronts and further configured to output the pseudo-phakic astigmatic component.

36. An apparatus for measuring astigmatic components of a patient eye during a real time vision correction procedure, comprising:
  a real-time intra-operative wavefront sensor configured to continually sample a first set of wavefronts returned from a patient eye during a first intra-operative time interval, where temporary surgically-induced factors that cause temporary changes to a pre-surgery measured astigmatic component of the patient eye occur during the first intra-operative time interval, where the first set of wavefronts is sampled after the removal of a crystalline lens of the patient eye putting the patient eye in an aphakic state, and with the real-time intra-operative wavefront sensor configured to output wavefront measurement data characterizing the first set of wavefronts; and a data processor, coupled to the real-time intra-operative wavefront sensor to receive the wavefront measurement data, configured to calculate an aphakic astigmatic component from wavefront data characterizing samples of the first set of wavefronts and to calculate a cornea-alone astigmatic component being a difference of the aphakic astigmatic component and a temporary astigmatic component, where the temporary astigmatic component is a measurement of the temporary astigmatic change caused by the temporary surgically induced factors, and with the data processor further configured to store the cornea-alone astigmatic component.

37. An apparatus for measuring astigmatic components of a patient eye during a cataract refractive surgery, comprising:
a real-time intra-operative wavefront sensor configured to continually sample a first set of wavefronts returned from a patient eye during a first intra-operative time interval, where temporary surgically-induced factors that cause temporary changes to a pre-surgery measured astigmatic component of the patient eye occur during the first intra-operative time interval, where the first set of wavefronts is sampled after the removal of a crystalline lens of the patient eye putting the patient eye in an aphakic state, and with the real-time intra-operative wavefront sensor configured to output wavefront measurement data characterizing the first set of wavefronts; and
a data processor, coupled to the real-time intra-operative wavefront sensor to receive the wavefront measurement data, configured to calculate a sphere component, an aphakic astigmatic component from wavefront data characterizing samples of the first set of wavefronts and to calculate a cornea-alone astigmatic component being a difference of the aphakic astigmatic component and a temporary astigmatic component, where the temporary astigmatic component is a measurement of the temporary astigmatic change caused by the temporary surgically-induced factors, and with the data processor further configured to output the sphere component and the cornea-alone astigmatic component.

38. The apparatus of claim 37 with the data processor further configured to:
output the sphere component and the cornea-alone astigmatic component during the refractive surgery.

39. The apparatus of claim 37 further comprising:
a display, coupled to the data processor, configured to display the sphere component and the cornea-alone astigmatic component.

40. An apparatus for measuring astigmatic components of a patient eye during a cataract refractive surgery, comprising:
means for continually sampling a first set of wavefronts returned from a patient eye during a first intra-operative time interval, where temporary surgically-induced factors that cause temporary changes to a pre-surgery measured astigmatic component of the patient eye occur during the first intra-operative time interval, where the first set of wavefronts is sampled after the removal of a crystalline lens of the patient eye putting the patient eye in an aphakic state, and for outputting wavefront measurement data characterizing the first set of wavefronts; and means, coupled to the means for continually sampling to receive the wavefront measurement data, for calculating an aphakic astigmatic component from wavefront data characterizing samples of the first set of wavefronts, for calculating a cornea-alone astigmatic component being a difference of the aphakic astigmatic component and a temporary astigmatic component, where the temporary astigmatic component is a measurement of the temporary astigmatic change caused by the temporary surgically-induced factors, and for outputting the cornea-alone astigmatic component.

41. The apparatus of claim 40 further comprising:
means for outputting the cornea-alone astigmatic component during the refractive surgery.

42. The apparatus of claim 40 further comprising:
means for displaying the cornea-alone astigmatic component.

43. The apparatus of claim 40 further comprising:
means for outputting the cornea-alone astigmatic component during the refractive surgery when the eye is in the aphakic state.

44. The apparatus of claim 40 further comprising:
means for outputting a first phakic corneal shape measurement of the patient eye taken before the first intra-operative time interval and before the crystalline lens is removed and for outputting a second phakic or aphakic corneal shape measurement of the patient eye taken during the first intra-operative interval; and
means for receiving the first phakic corneal shape measurement and the second phakic or aphakic corneal shape measurement and for calculating the temporary astigmatic component based on the first phakic corneal shape measurement and the second phakic or aphakic corneal shape measurement.

45. The apparatus of claim 44 further comprising:
means for attaching or integrating the apparatus of claim 44 with a surgical microscope.

46. The apparatus of claim 40 further comprising:
means for sampling a second and a third set of wavefronts, where the second set of wavefronts is returned from the patient eye before the first intra-operative time interval and before the removal of the crystalline lens when the patient eye is in a phakic state and where the third set of wavefronts is returned from the patient eye during the first intra-operative time interval and with the patient eye in the phakic state, and for outputting wavefront measurement data characterizing the second and third sets of wavefronts; and
means for calculating first and second phakic astigmatic components from the wavefront data characterizing the second and third sets of wavefronts and for calculating the difference between the first and second phakic astigmatic components to obtain the temporary astigmatic component.

47. The apparatus of claim 40 further comprising:
means for sampling a fourth set of wavefronts, where the fourth set of wavefronts is returned from the patient eye during the first intra-operative time interval and is sampled after implantation of an intra-ocular lens when the patient eye is in a pseudo-phakic state and for outputting wavefront measurement data characterizing the fourth set of wavefronts; and
means for calculating a pseudo-phakic astigmatic component from the wavefront data characterizing the fourth set of wavefronts and for outputting the pseudo-phakic astigmatic component.

48. The apparatus of claim 40 further comprising:
means for attaching or integrating the apparatus of claim 40 with a surgical microscope.

49. The apparatus of claim 40 further comprising:
means for calculating an anticipated post-surgery astigmatic component being the summation of the cornea-alone astigmatic component and a surgeon-induced astigmatic component and for outputting the anticipated post-surgery astigmatic component during the cataract refractive surgery.

\* \* \* \* \*